US010537466B2

United States Patent
Palazzolo et al.

(10) Patent No.: US 10,537,466 B2
(45) Date of Patent: Jan. 21, 2020

(54) DETECTING AND RESPONDING TO PRESHIVERING

(71) Applicant: Zoll Circulation, Inc., San Jose, CA (US)

(72) Inventors: James Palazzolo, San Jose, CA (US); Richard A. Helkowski, Redwood City, CA (US); Gary A. Freeman, Chelmsford, MA (US)

(73) Assignee: Zoll Circulation, Inc., San Jose, CA (US)

( * ) Notice: Subject to any disclaimer, the term of this patent is extended or adjusted under 35 U.S.C. 154(b) by 881 days.

(21) Appl. No.: 14/783,912

(22) PCT Filed: Apr. 8, 2014

(86) PCT No.: PCT/US2014/033339
§ 371 (c)(1),
(2) Date: Oct. 12, 2015

(87) PCT Pub. No.: WO2014/168952
PCT Pub. Date: Oct. 16, 2014

(65) Prior Publication Data
US 2016/0058613 A1 Mar. 3, 2016

Related U.S. Application Data

(60) Provisional application No. 61/810,508, filed on Apr. 10, 2013.

(51) Int. Cl.
*A61F 7/12* (2006.01)
*A61B 5/0488* (2006.01)
(Continued)

(52) U.S. Cl.
CPC .............. *A61F 7/12* (2013.01); *A61B 5/0488* (2013.01); *A61B 5/4836* (2013.01); *A61B 5/725* (2013.01);
(Continued)

(58) Field of Classification Search
CPC combination set(s) only.
See application file for complete search history.

(56) References Cited

U.S. PATENT DOCUMENTS 6,572,638 B1  6/2003  Dae et al.
7,127,278 B2 * 10/2006  Melker ................ A61B 5/0873
                                          600/340
(Continued)

FOREIGN PATENT DOCUMENTS

EP   1212000 B1   1/2006
JP   H11 347008 A  12/1999
(Continued)

OTHER PUBLICATIONS

PCT International Search Report dated Nov. 17, 2014 in related PCT Application No. PCT/US2014/033339.
(Continued)

*Primary Examiner* — Joseph A Stoklosa
*Assistant Examiner* — Adam J Avigan
(74) *Attorney, Agent, or Firm* — Fish & Richardson P.C.

(57) ABSTRACT

A method of reducing the likelihood of shivering comprises monitoring at least one physiological characteristic in a human or animal subject to detect preshivering and acting to reduce the likelihood of shivering when preshivering is detected.

14 Claims, 8 Drawing Sheets

(51) Int. Cl.
*A61B 5/00* (2006.01)
*A61F 7/10* (2006.01)
*A61F 7/00* (2006.01)

(52) U.S. Cl.
CPC ............... *A61B 5/746* (2013.01); *A61F 7/10* (2013.01); *A61F 2007/0054* (2013.01); *A61F 2007/0056* (2013.01); *A61F 2007/126* (2013.01)

(56) References Cited

U.S. PATENT DOCUMENTS

| | | | |
|---|---|---|---|
| 8,231,664 B2 | 7/2012 | Kulstad et al. | |
| 8,343,202 B2 | 1/2013 | Magers | |
| 2006/0190066 A1* | 8/2006 | Worthen | A61F 7/12 607/105 |
| 2009/0131835 A1 | 5/2009 | Voorhees et al. | |
| 2010/0087900 A1* | 4/2010 | Flint | A61B 5/1101 607/104 |
| 2012/0083672 A1* | 4/2012 | Cui | A61B 5/01 600/301 |
| 2014/0222121 A1* | 8/2014 | Spence | A41D 13/005 607/104 |

FOREIGN PATENT DOCUMENTS

| | | |
|---|---|---|
| WO | WO2004/064632 A1 | 8/2004 |
| WO | WO2010/042738 A2 | 4/2010 |
| WO | WO2012/052882 A1 | 4/2012 |
| WO | WO2013/013059 A1 | 1/2013 |

OTHER PUBLICATIONS

Supplementary European Search Report dated Nov. 25, 2016 in related European Application No. 14783023.6.
Office Action dated Dec. 3, 2018 in corresponding European Patent Application No. 14783023.6.

* cited by examiner

DETECTING AND RESPONDING TO PRESHIVERING

RELATED APPLICATION

This application is a 35 U.S.C. § 371 national stage of PCT International Patent Application No. PCT/US2014/033339 filed Apr. 8, 2014, which claims priority to U.S. Provisional Patent Application No. 61/810,508 filed Apr. 10, 2013, the entire disclosure of each such prior application being expressly incorporated herein by reference.

TECHNOLOGICAL FIELD

Embodiments of the present invention relate generally to detecting and responding to preshivering in a subject.

BACKGROUND

Under ordinary circumstances, the thermal regulatory system of the human body maintains a near constant temperature of about 37° C. (98.6° F.). This temperature is termed normothermia. Normothermia is generally optimum for efficient function of a healthy human.

The human body maintains normothermia through a number of very precise mechanisms that function to cool the body if it warms to far above normothermia, or to warm the body if it is becoming too cool. Normal cooling mechanisms may include, for example, dilation of the capillary beds exposed to the elements to enhance loss of heat from the body (peripheral vasodilatation), and sweating to create evaporative heat loss which, especially in combination with peripheral vasodilatation, can result in significant heat loss. If the body becomes too cool, on the other hand, the body has mechanisms that maintain warmth for the critical functions and to protect vital organs that include sequestering blood in the body's core to protect the vital organs, for example by AV shunting and capillary constriction in capillary beds exposed to the environment. Additionally, the body may shiver to produce additional metabolic heat.

SUMMARY

A method of reducing the likelihood of shivering, the method comprising: monitoring at least one physiological characteristic in a human or animal subject to detect preshivering; and acting to reduce the likelihood of shivering when preshivering is detected. The method can include one or more of the following features.

The at least one physiological characteristic comprises muscle tone.
The at least one physiological characteristic comprises breathing rate.
The at least one physiological characteristic comprises pulse.
The at least one physiological characteristic comprises oxygen consumption.
The at least one physiological characteristic comprises oxygen consumption in at least part of the body.
The at least one physiological characteristic comprises oxygen consumption in an upper extremity.
The at least one physiological characteristic comprises oxygen consumption in the torso.
The at least one physiological characteristic comprises monitoring spontaneous nerve activity.
Said monitoring farther comprises: generating a series of data points over time, said data points representing the at least one physiological characteristic; and analyzing the data points using at least one mathematical analyzing method taken from the group comprising: mean, mode, auto-regressive moving average, or change point analysis techniques comprising at least one of Basseville, Schuhart, Kalman estimation, and particle filters.
Acting comprises delivering a visual signal.
The visual signal is a message on a screen.
The visual signal is a warning light.
Acting comprises delivering an audio signal.
The audio signal is a verbal message.
The audio signal is sounding an alarm.
Acting comprises performing a task on the subject.
The task comprises delivering a drug.
The task comprises warming the subject.
The act of warming the subject comprises administering warm fluid.
The warm fluid is a liquid.
The warm liquid is administered orally.
The warm liquid is warm IV fluid.
The warm fluid is warm breathing gas.
The method of warming is the application of a warming blanket.
Warming the subject comprises warming an appendage.
Warming the subject comprises warming the blood of the subject.
Warming the blood comprises using an external blood warmer.
Warming the blood comprises using a heart-lung machine.
Warming the blood comprises using a dialysis machine.
Warming the blood comprises using an endovascular heat exchanger.
Said acting is performed automatically without human intervention.
A method of reducing the likelihood of shivering of a subject, the method comprising: cooling the subject; monitoring a physiological characteristic to detect preshivering; and acting in response to a determination of preshivering. The method can include one or more of the following features.
The method of cooling comprises exposure to ambient temperature.
The method comprising administration of a substance that reduces normal physiological temperature control.
The substance comprises an anesthesia.
The substance comprises a sedative.
Said cooling comprises external cooling.
Said cooling comprises cold surface wraps.
Said cooling comprises placing the subject on a cooled surface.
Said cooling comprises application of cold fluid.
The fluid comprises a breathing mist.
The mist is directed to the lungs.
The mist is directed to the nasal cavity.
The fluid comprises an IV fluid.
The application of cold fluid comprises applying a fluid to the surface of the subject.
Said applying comprises performing an alcohol rub.
Said cooling comprises blood cooling.
Said blood cooling comprises use of a blood by-pass device.
The blood by-pass device is a heart-lung machine.
The blood by-pass device is a dialysis machine.
The blood cooling comprises intravascular cooling.
Said cooling comprises application of a cold breathing gas.

Said cold breathing gas comprises heliox.

The cold breathing gas comprises a nebulized mixture.

Said cooling comprises performing lavage.

The lavage is gastric lavage.

The lavage is bladder lavage.

The lavage is peritoneal lavage.

The physiological characteristic monitored comprises muscle tone.

The physiological characteristic monitored comprises pulse.

The physiological characteristic monitored comprises breathing rate.

The physiological characteristic monitored comprises oxygen consumption.

The physiological characteristic monitored comprises oxygen consumption in part of the body.

The physiological characteristic monitored comprises oxygen consumption in an upper extremity.

The physiological characteristic monitored comprises oxygen consumption in the torso.

The physiological characteristic monitored comprises spontaneous nerve activity.

Said monitoring comprises generating data representing the physiological condition monitored, generating a series of data points and analyzing the data points using mathematical analyzing methods taken from the group comprising: mean, mode, auto-regressive moving average, or change point analysis techniques such as Basseville, Schuhart, Kalman estimation, particle filters.

Said acting comprises delivering a visual signal.

The visual signal comprises a message on a screen.

The visual signal comprises a warning light.

Said acting comprises delivering an audio signal.

The audio signal comprises a verbal message.

The audio signal comprises an alarm.

Said acting comprises performing a task.

Said task comprises delivering a drug.

Said task comprises warming the subject.

Said warming the subject comprises administering warm fluid.

The warm fluid is a liquid.

The liquid is administered orally.

The liquid is warm IV fluid.

The fluid is warm breathing gas.

The warming is the application of a warming blanket.

The warming is warming an appendage.

The warming the subject comprises warming the blood of the subject.

The warming the blood comprises using an external blood warmer.

The warming the blood comprises using a heart-lung machine.

The warming the blood comprises using a dialysis machine.

The act is performed automatically without the need for human initiation.

The subject has suffered a cardiac arrest.

The subject has suffered stroke.

The subject has suffered a traumatic

The injury is a brain injury.

The injury is a spinal injury.

The subject has suffered a myocardial.

The subject is undergoing surgery.

The surgery comprises brain surgery.

The surgery comprises heart surgery.

The surgery comprises kidney surgery.

The surgery comprises spinal surgery.

The surgery comprises back surgery.

The subject has recently undergone abdominal surgery.

The subject is receiving drugs which are temperature-sensitive.

The drugs administered are chemotherapy drugs.

The subject is receiving treatment for a heart condition.

The subject is receiving treatment for a kidney disorder.

The subject is receiving radiation therapy.

The subject is a burn victim.

The subject is being treated for battle injuries.

A system for reducing the likelihood of shivering, the system comprising: a subject cooling device; sensor for monitoring at least one physiological characteristic and generating data representing said at least one characteristic; a compiler for receiving and analyzing said data representing said characteristic from said sensor and making a determination whether preshivering exists; and a means for acting on said determination. The system can include one or more of the following features.

Said sensor comprises a skin sensor connected to an EMO machine.

Said sensor comprises a pulse meter.

Said sensor comprises an oxymeter.

Said compiler comprises a programmable computer.

Said cooling device comprises an endovascular cooling system.

Said cooling system comprises a surface cooling device.

Said surface cooling device comprises cooling blankets.

Said cooling system comprises a system for delivering cold fluid.

Said system for delivering cold fluid comprises a means for delivery of cold IV fluid.

Said system for delivering cold fluid comprises a system for delivery of cold breathing gas.

Said system for delivering cold fluid comprises a system for delivery of cold gas to the nasal cavities.

Said system for delivering cold fluid comprises a system for delivery of cold nebulized fluid to the nasal cavities.

The means for acting is selected from group comprising: an alarm, a message screen, a drug pump, a warning light, means of control of an endovascular cooling system, and a means of warming a subject.

A method for detecting preshivering in a subject undergoing cooling, the method comprising: a) stimulating a nerve of the subject; b) sensing a response resulting from said stimulation; c) recording data representing said response; d) cooling said subject; e) repeating steps a-c; f) deriving a nominal value for data received in several repetitions of step c); g) comparing the data received from the most recent repetition of step c) to said nominal value to make a determination whether change has occurred; and h) acting in response to said determination. The method can include one or more of the following features.

The cooling comprises exposure to ambient temperature.

The cooling comprises induced cooling.

The cooling is induced by infusing cold IV fluid.

The step of cooling includes infusion of cold IV fluid with a power infuser.

The cooling comprises use of an intravascular cooling system.

Said determination is that no change has occurred and wherein acting comprises waiting a predetermined period of time and then repeating all steps in said method.

Said determination is that change has occurred and wherein the step of acting includes taking an action taken from the group comprises: reducing the rate of cooling, stopping cooling, initiating anti-shivering mechanisms, increasing the anti-shivering methods, sounding an alarm, providing a visual alert, or transmitting a signal to a control unit which controls said cooling.

The data representing said response comprises the amplitude of said response.

The method comprises determining the latency of said response, and wherein the data representing said response comprises the latency of said response.

The method comprises determining the refractory period of said response, and wherein the data representing said response comprises the refractory period.

The method used in comparing said data is taken from the group comprising: mean, mode, auto-regressive moving average, or change point analysis techniques such as Basseville, Schuhart, Kalman estimation, particle filters.

The step of comparing said data comprises using more than one method taken from the group comprising: mean, mode, auto-regressive moving average, or change point analysis techniques such as Basseville, Schuhart, Kalman estimation, particle filters.

The method comprises the step of wirelessly transmitting said data to a location distal from said subject.

The method comprises the step of analyzing said data at said distal location, comparing at said distal location, making said determination at said distal location, and transmitting Said determination to a location proximal to the subject.

The method comprises the step of wirelessly transmitting said determination to a location distal from said subject.

Said stimulating comprises using a magnetic stimulator.

Said magnetic stimulator is located over the motor cortex and the sensing occurs at the abductor digiti minimi.

Said magnetic stimulator is located over T1-T11 and the sensing occurs at the rectus abdominis.

Said magnetic stimulator is located over Erb's Point and the sensing occurs at a location selected from the group comprising the abductor digiti minimi, the bicep and the triceps.

Said magnetic stimulator is located over C5-C6 and said response comprises pressure selected from the group comprising gastric pressure, esophageal pressure, and diaphragm pressure.

Said magnetic stimulator is located over the head and the sensing occurs on the face.

Said magnetic stimulator is located over face below the ear and the sensing occurs at the ipsilateral nasalis.

Said magnetic stimulator is located over the lumbo sacral region and the sensing occurs at the lower limbs.

Said stimulating is performed using surface electrodes.

The stimulation occurs at Erb's Point and the sensing occurs at the abductor digiti minimi.

The stimulation occurs at the wrist and the sensing occurs at the abductor digiti minimi.

Said stimulating is performed using needle electrodes.

A method for detecting preshivering in a subject that has suffered cardiac arrest, the method comprising: a) applying resuscitation efforts to the subject; b) stimulating a nerve of the subject; c) sensing a response resulting from said stimulation; d) recording data representing a response to said stimulation; e) repeating steps b)-d); f) deriving a nominal value for the data received in several prior repetitions of step d); g) comparing the value received from the most recent repetition of step d) with said nominal value to make a determination if a change has occurred; and h) acting in response to said determination. The method can include one or more of the following features.

The method comprises the step of cooling the subject.

A device for detecting preshivering in a subject, the device comprising: a stimulator for stimulating a nerve of a subject; a sensor capable of detecting a response resulting when said nerve of the subject is stimulated and generating data representing at least part of said response; a data analyzing device, said data analyzing device capable of receiving data from said sensor, compiling said data from a series of responses generated, determining a nominal value for said series, determining when change has occurred between said nominal value and said data, and transmitting a signal representing said determination. The device can include one or more of the following features.

Said stimulator is an electrode.

Said stimulator is a magnetic stimulator.

Said magnetic stimulator is in a circular configuration.

Said magnetic stimulator is in a torus configuration.

Said magnetic stimulator is in a FIG. 8 configuration.

Said magnetic stimulator is in a four leaf clover configuration.

Said device further includes a mechanism for mounting said stimulator on the body of the subject.

Said mechanism is a strap.

Said mechanism is a glove like device with a receptacle for a finger of the subject.

Said mechanism further comprises said sensor, such that when said mechanism is mounted on said subject, both sensor and stimulator are mounted on said subject.

Said mechanism for mounting further includes a body support board and wherein said stimulator is a magnetic stimulator and wherein said magnetic stimulator is embedded in said body support board.

The device comprises an automatic resuscitation unit, wherein when said subject is placed on said resuscitation unit, said stimulator and said sensor are automatically positioned.

Said sensor is attached to said body support board.

The device comprises a system for administration of therapeutic hypothermia, said system including a controller for controlling the administration of hypothermia, and wherein said signal comprises instructions for action by said controller.

Said instructions to said controller comprises instructions to continue cooling at the same rate.

Said instructions to said controller comprises instructions to reduce the rate of cooling.

Said instructions to said controller comprises instructions to warm the subject.

The device comprises including a wireless communication device, said communication device transmitting data compiled from said sensor to said analyzer.

The device comprises including a means to act, that means to act selected from a group comprising a means to: issue an auditory signal, issue a visual signal, and perform an act upon the subject.

The act upon the subject is taken from the group comprising: warm the subject or administer anti-shivering substance.

A method of detecting whether a moribund subject has regained relatively intact neural response and detecting preshivering comprising: a) stimulating a nerve of the subject; b) sensing a response from resulting from said stimulation; c) if no response is detected, waiting a period of time and repeating steps (a) and (b); d) if a response is detected, providing a signal; e) stimulating a nerve of the subject; f) sensing a response from resulting from said stimulation; g) recording data representing said response; h) cooling said subject; i) repeating steps a-c; j) deriving a nominal value for data received in all repetitions of step c); k) comparing the data received from the most recent repetition of step c) to said nominal value to make a determination whether change has occurred; and l) acting in response to said determination. The method can include one or more of the following features.

The method of stimulating is magnetic stimulation.

The subject is supported by a resuscitation board and said magnetic stimulation is by means of a magnetic stimulator located in said resuscitation board.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION

Figure 1A:
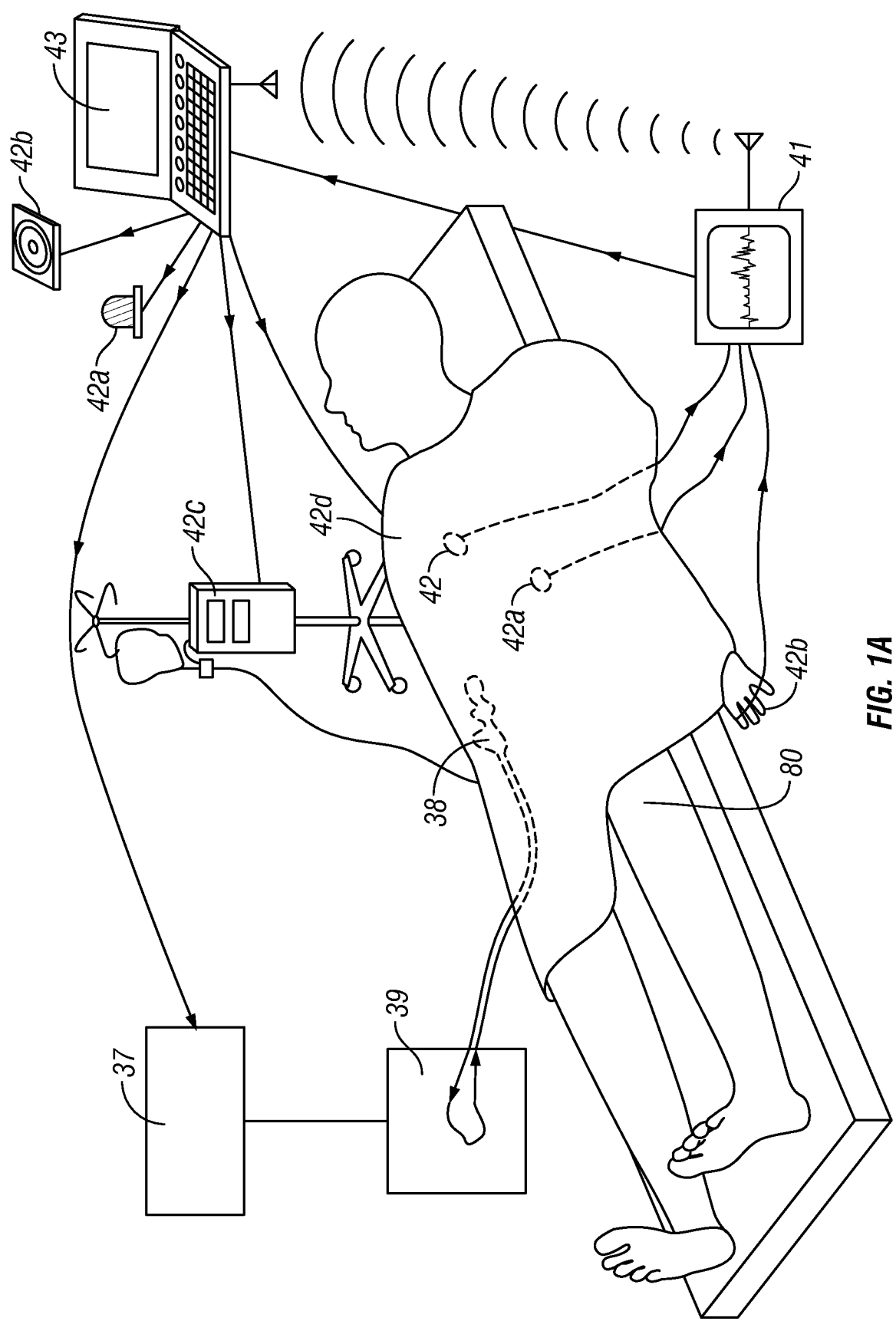
FIG. 1A is a representation according to an example embodiment of the invention.

Hypothermia is a condition of abnormally low body temperature generally characterized by a core body temperature of 36° C. or less, and may be further clinically defined according to its severity. For example, a body core temperature within the range of 32° C. to 35° C. may be described as mild hypothermia, 30° C. to 32° C. as moderate hypothermia, 24° C. to 30° C. as severe hypothermia, and a body temperature of less than 24° C. may constitute profound hypothermia. Although the above ranges may provide a useful basis for discussion, they are not absolutes and definitions vary in use in the medical literature.

Although normothermia is generally desirable and even mild hypothermia in conscious subjects may provoke vigorous thermoregulatory defenses which are potentially harmful in fragile subjects, in some cases hypothermia may be induced, and/or maintained in a subject for therapeutic purposes. By way of example, one such case is the protection of neural tissue, particularly protection from damage from hypoxia. Hypoxia may occur due to interruption of breathing, such as with drowning, or compromised circulation as in the case of cardiac surgery or heart attack, or the complete cessation of circulation, such as the case of cardiac arrest. In treating such cases hypothermia may be intentionally induced and may be maintained for some period of time.

As stated above, neural tissue in particular is prone to damage from hypoxia. Even when an episode of hypoxia does not result in death, it may result in severe residual brain damage. It has been found that in such cases the neural tissue benefit from the induction of hypothermia, often with maintenance of hypothermia for some period after hypoxic event such as cardiac arrest, usually for a duration of several hours to several days.

The mechanism of this neuroprotection is not fully elucidated, but may occur through one or a combination of several mechanisms including the blunting of post-insult elevation of neurotransmitters such as glutamate, reduction of cerebral metabolic rate, moderation of intracellular calcium, prevention of intracellular protein synthesis inhibition, reduction of free radical formation as well as other enzymatic cascades and even alteration of genetic responses to the hypoxic event.

Much damage may occur when the cells begin to receive warm, oxygenated circulation again. The cells may be exposed to damaging products of other cells that had been anoxic, which products then begin to circulate, and the sudden introduction of more oxygen into the chemical milieu that exists may cause even more damaging chemical products to form. This so called reperfusion injury might be minimized or even avoided if the subject is hypothermic at or soon after reperfusion.

The method of inducing hypothermia and maintaining hypothermia in a therapeutic setting has evolved in recent years. Originally total immersion in ice water was used. This method was clumsy, messy, time consuming and often incompatible with other treatment that required access to the subject, and was not well controlled, often resulting in problems such as serious over cooling and lack of temperature control. Further it involved so much discomfort that it was generally not available for conscious subjects. Subsequently cooling by alcohol bath and ice rubs was used, but these methods were very labor intensive and not very efficient, in part because the body's natural defenses against cooling, and were not capable of very precise control over the temperature range that the physician sought to obtain.

When the heart-lung pump began to be used for heart surgery, blood heating/cooling mechanisms in that machine made it possible to rapidly cool the blood and rather precisely control the subject's temperature. In addition, since the subject was generally under anesthesia and paralyzed, shivering during cooling was not a problem. However, such a machine was generally not employed for a long period of time because damage to the blood and less than perfect oxygenation that could lead to neural damage. Many surgeons preferred to keep the time a subject was on the pump to 4 hours or less to avoid brain damage, sometimes referred to as "pump head". Additionally it was only available in the most extremely invasive situations, such as during open heart surgery, with highly trained and specialized personnel present, and at great expense.

More recently, other effective methods of inducing and maintain hypothermia have been developed. For example, cooling blankets have been used. Tents for circulating cold air over a body have been devised. In some cases, vacuum has been placed over extremities, and then cool air has been circulated around those extremities. Cold breathing gases, and breathing mixture of gas and ice particles have been used as a cooling technique. These may be introduced into the lungs, or into the highly vascularized nasal cavities. Cold breathing gases with enhanced heat extraction characteristics, such as heliox gas, have been used. Cold IV fluid has been introduced into subjects to cool them. Cooling the blood directly during kidney dialysis has been proposed when the subject is undergoing treatment for kidney disease and hypothermia is desired. Even cold gastric, bladder or peritoneal lavage has been used as cooling techniques. All of these techniques have been used or proposed with varying degrees of success and providing varying degrees of speed of achieving hypothermia and control over the cooled subject's temperature.

A particularly useful cooling mechanisms, especially for achieving hypothermia quickly and maintaining it at a very precise temperature for a relatively long period, is the use of an intravascular cooling system. Such a system may have an intravascular heat exchanger, for example a cooling catheter which is insertable into the inferior vena cava (IVC) and in contact with the subject's bloodstream. Cold fluid may circulate within the cooling catheter and then into an external cooler/controller for removing heat from the cooling liquid. This cooling catheter and circulating cooling liquid are controlled by a controller unit that may have feedback from a temperature monitor that monitors the subject's temperature. These systems are capable of rapidly achieving a hypothermic target temperature and maintaining that temperature. Some particularly effective systems capable of rapidly achieving hypothermia to a level of 34° C. (in less than 30 minutes) and maintaining that temperature within a few tenths of a degree for days at a time. One such system is the Thermogard XP® available from ZOLL Medical Corporation.

Some terms useful in discussing induced in hypothermia include: (1) target temperature, the temperature the system is designed and programmed to achieve; (2) set point, the temperature subjects maintain at equilibrium. In a body at equilibrium in normothermia the set point is generally normothermia and the set point is set by the body's thermoregulatory mechanisms. In a body maintained under therapeutic hypothermia, the set point is generally the target temperature and is set by the system or personnel maintaining hypothermia; and (3) shivering threshold, the temperature at which a subject begins to shiver. In healthy subjects, the shivering threshold is generally 35.8°±C.

There are many purposes for which induced hypothermia may be clinically indicated. For example, after a subject has suffered a heart attack, a period of hypothermia may limit the damage suffered by the cardiac muscle due to hypoxia. A subject that has suffered a stroke may benefit from a period of hypothermia if that is initiated soon after the portion of the brain begins to experience vascular insufficiency. This would be true, unlike many current treatments, for both ischemic and hemorrhagic stroke. In brain surgery, back surgery, kidney surgery or in heart surgery, hypothermia may provide significant protective effect for the brain and other neural tissue, and the rest of the body, for example the spine and the heart, or even the kidney. Although a subject on a heart-lung machine, for example for open heart surgery, may have the blood cooled directly and the temperature controlled very well, not all brain surgery subjects are on heart-lung machines, and increasingly, even heart surgery involves beating heart surgery in which the subject is not on a heart-lung machine, and in those cases some other means of inducing hypothermia is needed such as the intravascular method described above. Besides use in surgery, it may be helpful to induce a particular body temperature other than normothermia for treatment, such as chemotherapy, where the drugs used are temperature sensitive and are most effective at temperatures other than normothermia. Trauma victims, such as accident victims or military personnel suffering battle injuries, may be helped by inducing hypothermia as well. In all these cases it may be necessary to cool the subject below the shivering threshold.

Unlike hypothermia induced in surgery such as open heart surgery or brain surgery where the subject is anesthetized and paralyzed, therapeutic hypothermia is now often induced in non-paralyzed subjects. In those cases shivering is a problem. Shivering produces a great deal of metabolic heat, as much as 600% above basal rate, making it very difficult, and indeed sometimes impossible to induce and maintain hypothermia. It is extremely uncomfortable for the subject, and has several harmful effects such as a negative impact on systemic oxygen consumption, often doubling or even that tripling oxygen consumption, and may cause hypoxemia, myocardial ischemia and even myocardial infarction in high risk subjects. This is especially a problem with post cardiac-arrest patents whose heart has just been resuscitated, or heart attack victims whose heart is often already compromised. Shivering may increase intracranial pressure, and if it continues for some time, may exhaust the subject and more than counteract any benefit of therapeutic hypothermia. It should be countered if a state of hypothermia below the shivering threshold is to be maintained for any length of time, and therapeutic levels of hypothermia are generally below the shivering threshold. Thus the control and prevention of shivering is one of the primary obstacles that must be dealt with to successfully provide therapeutic hypothermia to human subjects.

Additionally, shivering control is sometimes necessary when cooling to a target temperature above normothermia. For example, with the advent of relatively accurate and convenient temperature control such as the endovascular system mentioned above, cooling a feverish subject to normothermia and maintaining normothermia for a long period of time, even days, may be a desirable treatment. For example, the American Heart Association has included maintaining normothermia in ischemic and hemorrhagic stroke victims as part of their clinical guidelines. Accordingly many neuro-critical care units have begun to include maintaining normothermia as part of their protocol for treating cerebral vascular injury. In such subjects, however, the subject may be febrile, which generally has the effect of raising the shivering threshold, sometimes raising it above normothermia. In such a situation shivering is undesirable for many reasons including extreme discomfort, secondary neuronal injury, increased mortality, and poor functional outcome, raising cerebral pressure, increasing systemic oxygen consumption, exhausting the subject, and making it difficult or impossible to accurately maintain normothermia, among other problems.

Shivering control may also be important in other situations where the subject is in danger of falling below the shivering threshold for some other reason. For example, after anesthesia for any reason, for example extended surgery, the subject is often still cold from exposure to ambient temperature while the anesthesia depressed the body's ability to generate sufficient metabolic heat to maintain normothermia, and the anesthetic's paralytic effect may wear off before the subject has regained normothermia. In such a case the subject may well begin to shiver. In another situation, a burn subject might lose much of one of the body's most important protections against losing body heat to ambient exposure, an intact skin surface, and hypothermia below the shivering threshold might become a serious problem. In both these examples, no activity need be taken unless it appears that shivering is likely. In the subject recovering from anesthesia, the point at which muscle function sufficient for shivering returns may not be clear, and may not occur until the subject has warmed above the shivering threshold. In such a case no intervention would be needed to prevent shivering, and it would be helpful to know this. In the case of burn victims, they are currently kept in very warm ambient environments to prevent excessive hypothermia. This however is extremely uncomfortable for the health personnel overseeing the subject. Warm, moist conditions are also hazards for infections, a real problem with burn victims. Therefore, it is desirable to keep the ambient temperature as cool as possible yet avoid shivering. Some method of alerting the medical personnel to the danger of impending shivering would be helpful.

Shivering generally occurs in a healthy subject when the subject's temperature falls below a certain temperature known as the shivering threshold. In a normal human subject, the shivering threshold is about $35.8 \pm 0.2°$ C., but may vary from individual to individual, and may vary within the same individual based on conditions and health. For example, as discussed above, sometimes when the subject is febrile, the shivering threshold actually goes up, occasionally even above normothermia. There is actually a shivering threshold zone, normally between the shivering threshold of $35.8°$ C. and $34°$ C., below which the subject shivers little if at all. However, since the target temperature for therapeutically induced hypothermia is often below the shivering threshold but within the shivering threshold zone, attaining such therapeutic hypothermia and maintaining that temperature generally dealing with shivering. Likewise maintaining normothermia or very mild hypothermia in stroke victims who may be febrile may require cooling below that subject's shivering threshold. Shivering therefore is a serious problem faced in several situations when applying therapeutic temperature control to non-paralyzed subjects.

Various schemes of preventing shivering have been employed. The subject is sometimes warmed directly on the surface, for example with warming blankets or warming lamps. The subject is sometimes given warm fluid orally or even IV. IV administration may be warming a solution that is already being administered, for example drugs or blood, or administering a warm fluid such as a saline solution specifically for that purpose. Sometimes warm breathing gases are provided. Sometimes just an appendage may be warmed, or just warming the face may suffice to fend off or reverse shivering. A warm breathing gas may be given to the subject. If the subject is being given oxygen, that mixture may be warmed. Just as in cooling, warmed gas having enhanced heat exchange ability such as warm heliox may be administered. If the subject is on a heart lung machine, or is having the blood removed and recirculated, for example in dialysis, the blood may be warmed. Blood warmers, where blood is being administered, for example after trauma, of are used to warm the blood before introduction into the subject. One common method used to avoid shivering during therapeutic hypothermia is the administration of pharmaceutical agents that blunt the thermoregulatory responses of the body and particularly shivering. If the subject is being intentionally cooled, for example with an endovascular cooling system as described above, the rate of cooling may be slowed or even reversed and the subject warmed, if shivering begins. Warming, slowing cooling rate, stopping cooling altogether, warming the face and warming the extremities have all been employed in various situations and with varying degrees of success. Since warming or stopping cooling is often at odds with the purposes of applying the therapeutic hypothermia in the first place, but might well become indicated if the subject begins to shiver, some means of alerting health care personnel to the fact that the subject is on the brink of shivering would be very helpful.

Whatever anti-shivering mechanisms are employed, it has been observed that once a subject begins to shiver, it is far more difficult (sometimes even impossible) to reverse the shivering and cool the subject to the desired body temperature than it would have been if shivering had been avoided altogether. It may require, for example, larger doses of the pharmaceutical agent to overcome the thermoregulatory responses than would have been necessary to avoid the shivering in the first place. It may end up requiring a longer time to reach target temperature, and accurately maintaining target temperature may be very difficult if shivering is allowed to begin. In the case where the target temperature is not necessarily below the shivering threshold, e.g. where the subject has a mild fever and normothermia is being maintained, or a burn subject is losing a great deal of body heat to the environment, it may be preferable to avoid giving the anti-shivering drugs merely as a prophylactic measure unless shivering is imminent, to give as little as possible. Thus knowing when shivering is imminent would be very helpful. Additionally, some signaling mechanism that shivering is imminent would be very useful since the attending health personnel may not be constantly present and should to be alerted if shivering is about to begin.

Since the shivering threshold varies from individual to individual, and from situation to situation, merely selecting a predetermined core temperature to initiate anti-shivering efforts may not work. A method to determine when a particular subject is about to begin shivering based on physiological information from that specific subject is needed. In some subjects it will be late, and those subjects may not be cooled as quickly as possible if anti-shivering efforts are initiated too early. It is important to cool as quickly as possible to therapeutic levels, so delaying cooling at all in the false belief that the delay is required to prevent shivering when no shivering is imminent would also not be ideal. For example during ambulance transportation, the ambulance personnel may avoid cooling merely to avoid invoking shivering when it might be desirable to cool the subject in anticipation of therapeutic cooling once the subject reaches the hospital. This is especially true since in the United States, physicians rarely ride in the ambulance bringing the subject to the hospital for treatment and thus initiation of anti-shivering drug administration cannot occur in the ambulance. Cooling the subject may include intravenous application of cold IV solutions. Although the trip to the hospital is typically not very long and induction of shivering would not be a significant problem with normal intravenous introduction of cold solution, recently applications of IV solutions including cold solutions has be accomplished by means of devices to enhance introduction of solution into the blood stream, such as the Power Infuser® by ZOLL Medical which can infuse sufficient cold saline in a sufficiently short time that rapid temperature reduction in the ambulance is possible. Achieving as rapid a cooling as possible yet avoiding shivering may require some means to detect the imminent on-set of shivering.

Since the anti-shivering agents are generally best administered 30 minutes to 10 minutes prior to rapid cooling, it would be helpful, even in the hospital after anti-shivering drugs had been administered to recognize when the subject was on the verge of shivering prior to full effect of the drugs and thus be able to reduce or cease cooling or take other anti-shivering steps to avoid crossing the shivering threshold. In short, it would be very helpful to be able to begin and proceed with cooling as soon and as quickly as possible, yet to avoid initiating shivering before the anti-shivering agents are administered and have fully taken effect. To do so, however, requires some means of obtaining physiological data from the subject that would indicate that the subject has entered a preshivering state.

A condition occurs as a body cools but shortly before it begins to visibly shiver which is sometimes called preshivering muscle tone or merely preshivering. In this condition the muscles begin to tense and the metabolic rate increase, sometimes as much as 200% above basal rate. In a healthy individual this generally occurs at body temperatures of about 36.0°. However no shivering is generally visible. If cooling of the body continues, however, the subject begins to shiver. Inception of this preshivering muscle tone may thus provide a signal that shivering is imminent and allow the helpful intervention mentioned above before visible shivering began. A method to detect this preshivering is thus needed.

Various physiological characteristics that may signal preshivering may include the muscle tone of the subject, especially in those areas where preshivering may first appear. This would include the upper extremities and the torso. The muscle tone may be recorded directly, for example by an EMG machine, and a sudden increase signal the appearance of preshivering. The pulse of the subject may be monitored for signs that preshivering muscle tone has appeared. The subject's breathing rate may reveal the appearance of that physiological characteristic. Spontaneous nerve activity, also measurable with the EMG, would provide data that could be used to determine the occurrence of preshivering. Slightly more complex, oxygen consumption could be monitored to provide data to determine when preshivering appears. This could be systemic oxygen consumption, or could be oxygen consumption in a particular part of the body such as the upper extremities or the torso. In those cases, the oxygen saturation of the arterial blood feeding that area could be monitored and the venous blood supply leaving that area monitored for example by a venous blood gas monitor, to give an oxygen consumption for that specific area. A relatively sudden increase could signal the appearance of preshivering muscle tension.

For a more complex determination, the subject's neural function may be determined and monitored. A useful tool for analyzing a subject's neural function is nerve conduction or evoked potentials. Nerve conduction data or evoked potentials are obtained by applying a stimulus to a nerve of the subject and detecting the resultant electrical signal at the muscle enervated by that nerve pathway. Traditionally the technique has been used to study the condition of a neural pathway in, for example, diagnosing and analyzing nerve compression injuries, or conducting a study of the central nervous system, for example in ALS and MS. However, such studies may also be used to analyze the condition of a subject's musculature for example atrophy or of importance to this invention preshivering muscle tension.

In obtaining an evoked potential, and specifically a muscle evoked potential (MEP), stimulation of the nerve may be by means of an electrode, either a needle electrode or a surface electrode, with an electrical impulse being delivered to activate the desired nerve. (Although MEP is most commonly used to refer to action potentials elicited by noninvasive stimulation of the motor cortex through the scalp, here the term MEP will be used to refer to all actions potentials evoked in the muscles as a result of a remote stimulation.) Needle and surface electrodes have the advantage of precision in selecting precisely what nerve to stimulate, but are primarily useful for the study of nerves available at or near the surface of the subject. In particular, the brain is generally not easily available for stimulation by surface electrodes because the electrical impulse is greatly attenuated by the scalp and skull and can only be effectively delivered to nerves no more than a few centimeters below the surface. To accomplish even that, a large, painful and sometimes dangerous shock is needed. Even electrical stimulation of nerves more readily accessible to the surface involves subject discomfort from the shocks.

More recently, painless magnetic stimulation that relies on induced eddy-current stimulation has gained wider acceptance and has generally replaced electric shock in the study of MEPs. Because it was originally developed to study stimulation of the brain and involved a magnetic stimulation applied to the head, it is often called Transcranial Magnetic Stimulation, or TMS. However magnetic stimulation may be used to induce evoked potentials from areas other than the brain, so here we will use the term magnetic stimulation to include transcranial stimulation and other stimulation.

The term magnetic stimulation has come to mean electrical stimulation from an eddy current induced by a magnetic field rather than direct stimulation by a magnetic field. Magnetic stimulation can excite not only the motor cortex of the brain, but also motor roots in the region of the intervertebral foramina, as well as peripheral nerves and plexuses. Although in the study of specific nerves, magnetic stimulation sometimes lacks the precision of placement of, for example needle electrodes, it has the advantage of generally being available to stimulate brain tissue and to stimulate surface nerves without inducing pain or damage. Where precision of placement of the stimulation is not as important, such a method is often ideal.

The magnetic stimulator is an electromagnetic placed over the portion of the body to be stimulated. A large current, perhaps 5,000 amps, is pulsed rapidly through a conductor, for example a circular coil, thereby generating a magnetic field. The current pulse is may be created by the discharge of a capacitors charged to, for example, 4 kV through a copper wire coil to generate a brief but intense magnetic field of up to 2 tesla. If a second conductor is in the vicinity (e.g. brain tissue) an electric field will be induced in a direction opposing the current flow in the primary conductor which is creating the magnetic field. At the interface between the coil and the secondary conductor, the electric field induced by the magnetic field is always zero in a radial direction at all depths and at any angulation of the coil Thus with a circular coil, the induced electric field can be thought of as concentric circles parallel to the plane of the interface. The time course of the induced electric field follows the first differential of inducing current and is instantaneously at maximum at the onset of inducing current flow.

When the coil is held to the head of the subject, the field penetrates the scalp and skull and induces a small current parallel to the plane of the coil in the adjacent second conductor (e.g. the brain). When the induced current is large enough, generally several mA/cm², depolarization of the neuronal membranes occurs, firing the nerve. In this way the nerve is activated and an evoked potential may be elicited without needing to apply a painful electric shock to the subject. Also, since the scalp and skull do not significantly attenuate the magnetic pulse, the stimulation may be applied to brain tissue more effectively than an electric shock applied to the skin of the scalp. In the same manner, a magnetic stimulator is able to stimulate nerves in other locations, for example the plexus at Erb's Point in the shoulder blade area or neck area of a subject or the spinal nerves at T1-T12, without the need to apply a painful electric shock.

The functioning of the magnetic stimulator is determined by several factors including coil construction and configuration. Different constructions and configurations are appropriate for different applications. A copper coil is generally preferred, surrounded by a plastic covering. Different alternatives in the construction of the coil include a so called air core design in which the core is comprised of an inert substance and a solid core design in which the coil possesses a ferromagnetically active material. The solid core design results in a more efficient transfer of electrical energy into a magnetic field with substantially reduced amount of energy dissipated as heat and so can be operated under more aggressive duty cycles often mandated in constant use where interruption to dissipate heat is not feasible.

Different geometric configuration of the coil may be used for different applications. A simple circular shaped coil is often used, for example, to stimulate the motor cortex. Other configurations that may be considered include a FIG. 8 coil sometimes called a butterfly coil, and a four leaf configuration useful for focal stimulation of peripheral nerves. The configuration of the coil affects the configuration of the magnetic field and thus of the area of induced current below that coil. As can be seen, such configurations can create focal areas below the coil for more precise stimulation where desired.

Location of desired stimulation, of course, differs depending on which muscle or group of muscles the operator desires to stimulate. Thus a 13 cm diameter circular coil produces a maximum induced current at its circumference and therefore, when placed with its center at the vertex of the motor cortex, the coil approximately overlays the hand area of the primary motor cortex. The hemisphere stimulated depends on the direction of the current in the coil. With monophasic current flowing predominately in a clockwise direction, the right hemisphere is excited and this stimulates a response that may be detected in the left hand muscles. Reversing the direction parent by inverting the coil for example, will preferentially excite the left hemisphere and thus may be detected in the right hand muscles. Biphasic stimulators with current flowing briefly in one direction and then the reverse direction excite both hemispheres sequentially. Stimulation of Erb's Point may be detected in the bicep or triceps. A magnetic stimulation of the spinal nerves at T1-T12 may be detected in the rectus abdominis. A magnetic stimulator properly located over the neck may be used to stimulate the phrenic nerve roots.

A figure eight coil in which the current in the two loops summate at the central segment has its maximum induced current under this central segment. To stimulate the hand area, therefore, the coil is placed some 5 cm lateral to the vertex. It has been shown that excitation is maximal when the coil is oriented about 45° from the parasagittal plane with coil current flowing from a posterior-lateral to anterio-medial. Angulated FIG. 8 coils where the two wings are not in the same plane are useful for stimulating the primary motor area for the legs. Using such a coil, however, requires some precision placement of the device, and precise placement may not be necessary for all applications as will be seen.

Preshivering generally occurs in the neck, torso, abdomen and shoulders before it presents in the extremities in a normal conscious or semi-conscious subject. These then are the areas of particular interest in the in-hospital subjects undergoing therapeutic hypothermia. However, in the largely comatose population of cardiac arrest victims cooled in the field, preshivering may be systemic and preshivering may be detected at any location.

Sensors for detecting a response resulting from the stimulation include surface electrical sensor similar to those used for ECG machines. Such sensors are understood to those of skill in the art, and the precise location of the sensor is well determined for most muscles useful for detecting MEPs.

Nerve conduction testing produces various useful data. One detectable characteristic of an MEP is velocity. When the time of the stimulation is known relative to the time of the evoked response, the time for the nerve stimulation to travel to the muscle and to evoke the response may be determined. This is generally termed latency of response, or just latency. Thus a stimulus is triggered at a certain time, and the resultant response time is recorded, the latency of that nerve transmission is then determined. A series of these can present an average latency for that particular stimulation/response and provide a data stream of latency values that may be analyzed, for example, to determine if the latency becomes different at some point. Latency will vary depending on the type of stimulation (magnetic stimulation may produce a latency a few milliseconds later than electrical stimulation at the same location on the scalp) and location (muscles closer to the stimulation, understandably, tend to respond sooner than muscles more distant,) and the size of the nerve stimulated (larger diameter nerves tend to transmit impulses faster, so a response along a nerve path that involves larger diameter nerves generally has a shorter latency). Nonetheless, if the same stimulation method and location for stimulation and same location for detection of the response is used for a series of stimulation/response pairs, they should produce reasonably consistent latency values unless some physiological condition changes, such as the inception of preshivering. Muscle tone, such as that which will be initiated with preshivering, may significantly change the latency, a change that may be detected to indicate the onset of preshivering. For purposes of this patent, a mere variation in data value does not necessarily represent change. The question whether change has occurred asks whether a significant difference has arisen that indicates an actual change in the physiological condition of the subject, not a merely different value of the data characteristic measured that is within the range of normal variation of that data characteristic without a change having occurred in the subject's physiological condition, and also if that difference represents preshivering.

Another characteristic of the response that may be particularly helpful is the amplitude of the response. Amplitude of the MEP is much greater if the subject produces some background muscle activity. This effect is called facilitation. For example, in hand muscles the subject only needs to produce 1-2% of their maximal force for the MEP to be facilitated by an order of magnitude. Proximal arm and leg muscles are less facilitated by background contractions but it is still sufficient to produce a marked effect, perhaps an order of magnitude for 10%-20% maximal background force of the muscle in question. Thus when the body develops increased muscle tension and tiny amounts of muscle action to produce heat, i.e. preshivering, dramatic alterations in the average amplitude of the MEP may be detected.

Another feature of nerve transmission that is useful is the refractory period. Immediately following depolarization, that portion of an axon where excitation occurred is completely unexcitable and cannot generate an action potential for a brief time. Within a few milliseconds, the axonal membrane becomes relatively excitable again and can produce an action potential, eventually fully returning to its resting level of excitability. By using a series of closely timed stimulations it may be determined how long it is before a stimulated nerve regains full excitability. By convention, the first excitation pulse is referred to as the conditioning stimulus. The second or test stimulus is then delivered at a predetermined interval. Those paired pulses may be delivered with the test stimulus at varying intervals until a time period may be determined as the length of time shorter than which the nerve cannot generate a subsequent impulse but longer than which it can. That time period is the refractory period of the nerve.

Another characteristic of the nerve pulse that results from stimulation is the width of the pulse. The width of the neural pulse (i.e. its duration) may change measurably due to varying factors, for example, basal motor neuron background firing rates are increasing prior to shivering onset, and pulse dispersion, which manifests as pulse widening therefore occurs. In seeking alterations in detectable data that may indicate change that signals preshivering, monitoring pulse width provides another measure that may be used.

A technique has been developed generally called the Triple stimulation technique to isolate the neural contribution by upper motor neurons to motor evoked responses using a series of three stimulations along a nerve transmission pathway to a particular muscle group. For example, a motor evoked potential in the abductor digiti minimi (ADM) which is in the little finger, is evoked by a series of timed stimulations; a trans-cerebral magnetic stimulation over the motor cortex, an electrical stimulation at Erb's point, and another electrical stimulation at the wrists. A recording of the response is taken from the ADM, abductor digiti minimi, the little finger. A timer is used to initiate the stimulations in a timed sequence to provide a collision of the evoked action potential at the desired location. Recording protocols have been defined for two muscles, the abductor digiti minimi (ADM) and the abducto hallucis (AH) (a foot muscle). The collision of the stimulations from the trans-cerebral stimulations and the stimulations further down the pathway toward the muscle to be stimulated may essentially isolate the effect of the trans-cerebral stimulation, and allow the detection and analysis of the effect of the other stimulations alone. This is potentially quite useful in attempting to detect change due to the appearance of preshivering rather than a condition directed by higher neural control, although it requires significantly more complex equipment and set-up than a single stimulation/response arrangement.

The techniques of evoked potential or nerve conduction described above may be used to determine a general status of the musculature enervated by the nerve root stimulated. When an initial baseline state is determined, for example prior to cooling, and the state is then monitored, it would then become possible to identify when change occurs and the nature and significance of that change.

Mathematical techniques may be used to analyze a data stream to determine if a change has occurred, what the nature of that change may be, what the significance level of that change may be, and with what degree of confidence can we say that a change has occurred. All of these factors may then be used to determine what if any action is appropriate. Generally, methods for detecting changes can include determining initial statistical characteristics any one or multiples of the nerve or muscle characteristics, and then analyzing those characteristics for any significant, sustained changes. For instance, the known techniques such as change point analysis such as that described by Basseville (Basseville M, Nikiforov IV. Detection of Abrupt Changes: Theory and Application. Engelwood, N.J.: Prentice-Hall 1993) or Pettitt (Pettitt AN. A simple cumulative sum type statistic for the change point problem with zero-one observations. Biometrika 1980; 67:79-84.) Other known methods such as Shewhart control charts may be employed for first detecting changes in the characteristics and then assessing whether the change detected is of a sufficient magnitude.

Methods such as the Kalman filter may be used for the estimation and prediction of the nerve and muscle state. The Kalman filter estimates a process by using a form of feedback control; the filter estimates the process state at some time and then obtains feedback in the form of (noisy) measurements. As such, the equations for the Kalman filter fall into two groups: time update equations and measurement update equations. The time update equations are responsible for projecting forward (in time) the current state and error covariance estimates to obtain the a priori estimates for the next time step. The measurement update equations are responsible for the feedback—i.e. for incorporating a new measurement into the a priori estimate to obtain an improved a posteriori estimate. The time update equations can also be thought of as predictor equations, while the measurement update equations can be thought of as corrector equations.

One of the primary limitations of the Kalman filter is that it only models a linear system with Gaussian distribution, not often encountered in the physiological setting. The best known algorithm to solve the problem of non-Gaussian, nonlinear filtering is the extended Kalman filter (EKF). This filter is based upon the principle of linearizing the measurements and evolution models using Taylor series expansions. The series approximations in the EKF algorithm can, however, lead to poor representations of the nonlinear functions and probability distributions of interest. As a result, this filter can diverge. Based on the hypothesis that it is easier to approximate a Gaussian distribution than it is to approximate arbitrary nonlinear functions other researchers have developed a filter termed the unscented Kalman filter (UKF). It has been shown that the UKF leads to more accurate results than the EKF and that in particular it generates much better estimates of the covariance of the states (the EKF often seems to underestimate this quantity). The UKF has, however, the limitation that it does not apply to general non-Gaussian distributions as is often the case with the ECG spectral distributions. Sequential Monte Carlo methods, also known as particle filters overcome this limitation and allow for a complete representation of the posterior distribution of the states, so that any statistical estimates, such as the mean, modes, kurtosis and variance, can be easily computed. Particle Filters can therefore, deal with any nonlinearities or distributions. Particle filters rely on importance sampling and, as a result, require the design of proposal distributions that can approximate the posterior distribution reasonably well. In general, it is hard to design such proposals. The most common strategy is to sample from the probabilistic model of the state's evolution (transition prior). This strategy can, however, fail if the new measurements appear in the tail of the prior or if the likelihood is too peaked in comparison to the prior.

Some implementations use an estimator/predictor trajectory tracking technique known as the Unscented Particle Filter (UPF) as developed by Merwe, Doucet, Freitasz and Wan.

The data concerning the original state of the subject and subsequent data indicating the subject's state may be collected and provided to a central analysis unit such as a programmable computer for analysis using any of the methods described. Besides analyzing the data to determine if change has occurred, such a device is generally also capable of selecting among possible responses and either directing such responses itself, for example an action by a device it controls such as a message screen, or alerting others to the appropriate action.

Referring to FIG. 1A, a subject 80 may be monitored for physiological characteristics that signal preshivering. For example, a sampling and receiving device 41 such as an EMG machine may monitor the torso to sample and compile data representing muscle tone, using sensor 42, or may monitor for spontaneous nervous activity using sensor 42a. Alternatively the data sampling and compiling device 41 may be connected to a sensor 42b such as an oxygen saturation sensor that can be used to determine oxygen saturation in the finger and thus provide a measure from which oxygen consumption in the arm may be determined. The sensor on the finger may also detect pulse. These sensors are examples of the type of sensors that may be used, but other may also be employed. A system need not have all these sensors, and need not sample to detect and compile each type of characteristic, depending which characteristic the operator desires to use to determine preshivering. Indeed, one may be used alone, or several may be used simultaneously.

If the subject is being cooled, a system for inducing hypothermia may be employed. For example, such a system may be an intravascular cooling system involving an intravascular cooling catheter 38 attached to an external heat exchanger 39 that may heat or cool heat exchange fluid that circulates in the catheter. The entire system is controlled by controller 37 that may set a target temperature for the subject, control the speed or temperature of the heat exchange fluid. The controller may also receive instructions from the analyzer device 43.

The data representative of the characteristic or characteristics being observed may be transmitted from the sampling and receiving device 41 to an analysis device 43. That transmission may be through a direct physical connection such as a wire, or may be transmitted wirelessly. The analytical device 43 may be, for example, a programmable computer. Alternatively the analytical device may be located in the same physical device as the sampling and receiving device.

The analytical device determines from the data whether preshivering exists. The analytical device then determines the action to be taken, and depending on the action deemed appropriate, may initiate that action. For example, no preshivering may be detected and the action chosen may be to determine the time period appropriate before the next data sampling, and the sampling device may be instructed to sample again after that period has passed. Alternatively, preshivering may be detected, and a visual signal sent out, for example a warning light 44a may be lit, or an audio signal may be initiated, for example an alarm sounded or message sent using speaker 44b, or written on a screen visible to the operator. The analytical device may even initiate action without human intervention, such as activating a drug pump 44c to deliver drugs to a subject through an IV already placed in the subject. It may initiate warming using a warming blanket 44d. These are examples of action initiated in response to a determination of preshivering are by way of example and not limitation. As with the sensing units, one, two or more of the actions may all be initiated in response to a determination of preshivering. Other possible sensing and responding methods have been described previously and could be employed as well.

The method of analysis may be direct analysis, for example a muscle tone of a certain level may indicate preshivering, or a certain pulse rate might be indicative. However, since most of the characteristics that are sensed vary from subject to subject, a method of monitoring the characteristic over time and responding to a variation in that characteristic that suggests preshivering is useful. One method of doing so involves recording a series of data points over time, using that stream of data points to generate a nominal value representing the average or usual data point, and then comparing the most recent data point with the nominal value. Various methods of analysis may be used, for example: mean, mode, auto-regressive moving average, change point analysis techniques such as Basseville, Schuhart, Kalman estimation, particle filters. These may identify a variation that indicates that change signaling preshivering has occurred. For example, a sudden increase in muscle tone may signal preshivering. Likewise a sudden increase in oxygen consumption may signal preshivering. It should be noted that several characteristics may be analyzed in conjunction to make the preshivering determination. For example, if pulse increased but no change in muscle tone was discerned, the analytical determination might be that no preshivering existed. Similarly oxygen consumption may increase with no increase in pulse thus suggestion preshivering even without directly monitoring muscle tone. Several physiological characteristics may change simultaneously that strongly indicate preshivering, for example increase in spontaneous nerve activity and increase in muscle tone and pulse together might create a very strong suggestion of the inception of preshivering.

Figure 1:
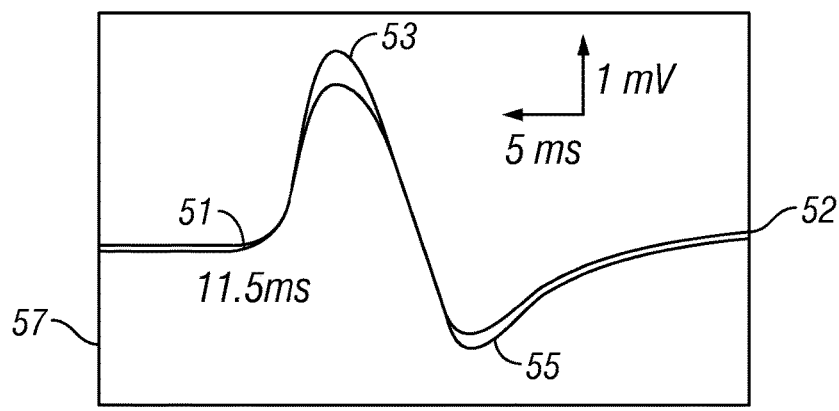
FIG. 1 is a representative tracing of an MEP according to an example embodiment of the invention.

The use of a muscle evoked responses (MEP) is one way to monitor a physiological characteristic to seek to determine preshivering. Referring now to FIG. 1, a representative tracing from an EMG machine is shown that depicts a muscle evoked potential (MEP) recorded from the Biceps brachii muscle using transcranial magnetic stimulation with a circular magnet located approximately over at the apex of the motor cortex. In the example shown, the amplitude of the MEP is the voltage from the peak 53 of the MEP to the lowest point 55 and in this example is approximately 4.5 mV. The latency is the period of time from the moment of stimulation 57 to the peak of the responsive MEP 53. The tracing shows a latency of approximately 11.5 msec. The MEP width, sometimes referred to as pulse width, may also be determined. In this example, the width is shown as the time from the beginning of the MEP until it returns to base level, or in this tracing, the time between onset of MEP 51 and the return to base line 52. Depending on the location of the stimulus, or the type of stimulus (e.g. electrical or magnetic) these values will vary. However, the actual values for the initial measurements are not critical. Of primary importance to this invention is that a consistent level of values is established and if, after cooling begins, the values change in a way that indicates that preshivering exists.

Figure 2:
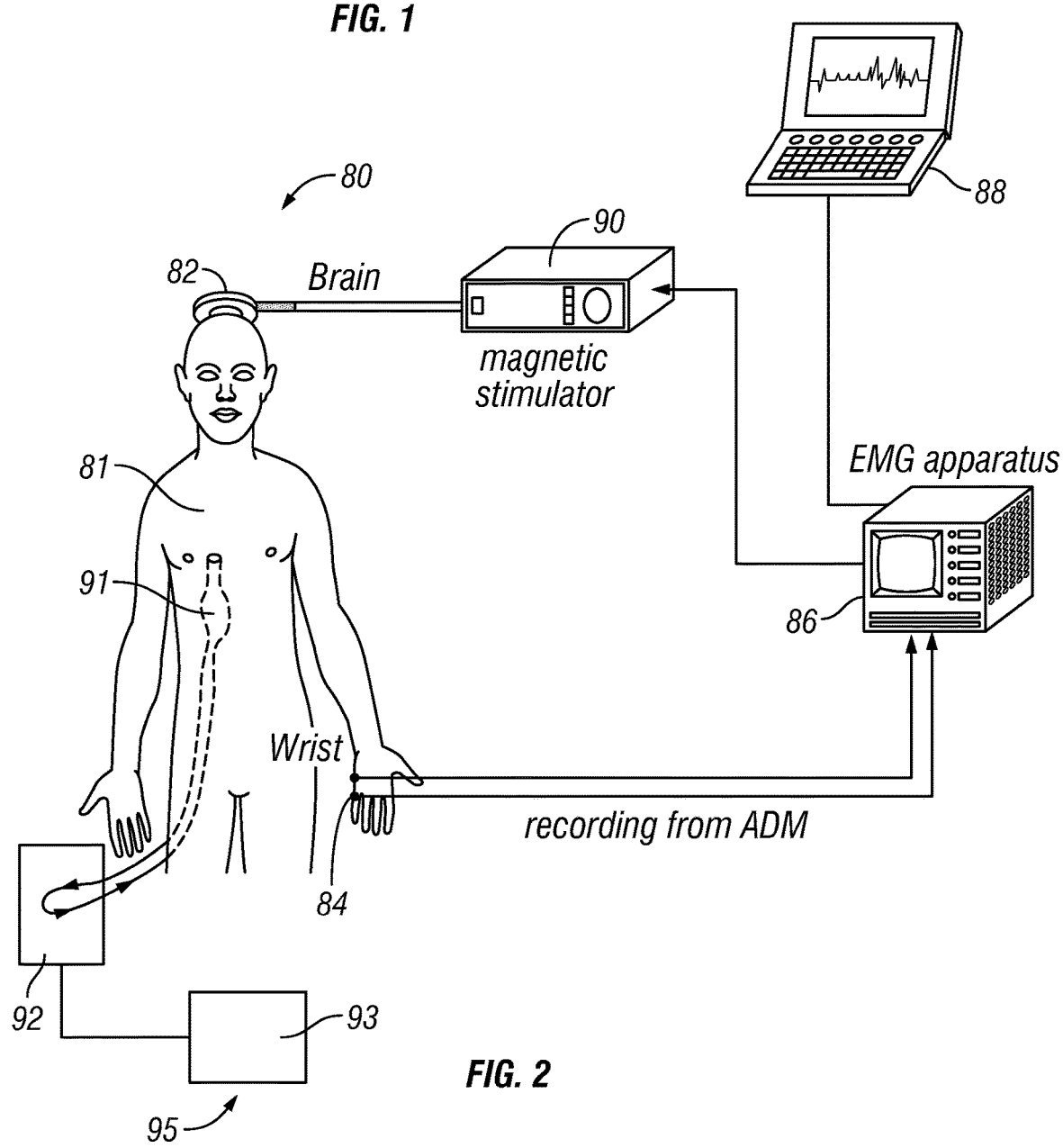
FIG. 2 is a depiction of the system of the invention with a magnetic stimulator over the head of a subject according to an example embodiment of the invention.

Referring now to FIG. 2, the system 80 designed for detecting preshivering in a subject 81 comprises a magnetic stimulator 82 positioned over the motor cortex of the subject to stimulate an MEP in the abductor digiti minimi detected there by a surface electrode sensor 84 which generates data representing that MEP. Although in this example, the MEP is generated in and sensed in the abductor digiti minimi, other locations may be used, such as the biceps brachii. An EMG 86 functions as both a triggering device to trigger the magnetic simulation and a data collection device for collecting the data representing the response. The necessary electrical circuitry for generating the electrical pulse that generates the magnetic pulse may be located in a separate device, here a magnetic stimulator activation device 90. The analyzing device 88 receives the data representing the response and compiles it and compares it to previously and subsequently generated data. That data may be, for example, the amplitude of the MEP. If the time of the triggering signal is noted and the time of the response is also noted, the velocity of the nerve transmission may be determined and the latency of the response determined. In that case, the latency or the velocity may be the data analyzed. If the subject is being cooled, a cooling system 95 comprising an internal heat exchanger such as a cooling catheter 91, an external heat exchange unit 92 such as a unit to heat or cool and circulate heat exchange fluid through the catheter and a controller 93 to control the system may be used.

A slightly more complex procedure involves determining the refractory period for a nerve. After a nerve is stimulated, the axon is not sensitive to a subsequent stimulation until enough time has passed for it to regenerate its ability to be stimulated. This time period is called the refractory period. To determine the refractory period, a series of triggering pulses may be generated by the stimulator in increasing time proximity, until two pulses are sent so closely spaced in time that there is no MEP produced by the second stimulation. To verify that this time period is the refractory period, a time is allowed to pass to permit the nerve to recovery the ability to be stimulated, and pair of stimuli are again sent as closely spaced as previously so that it may be confirmed that no MEP is generated by the second stimulus. When this is confirmed, the time period may be termed the refractory period. A series of refractory periods may be generated to determine if the current refractory period, when compared to previous refractory periods, indicates if change has occurred. The apparatus for determining the refractory period (not illustrated) may be essentially the same MEP generating apparatus shown in FIGS. 2-5, for example, but with an added timing device operating to time the stimulating pulses. Of course that timing mechanism may be built into the EMG, or may be directed by an external device such as a computer. As a practical matter, the timing may be controlled by programing within the EMG itself or by the same computer device that is compiling and analyzing the data.

The analyzing device may be, for example, a computer that can compile a series of responses and determine a nominal value for some characteristic of those responses, for example amplitude or latency, and when a new response is generated, compare that characteristic of the new response to that nominal value to detect a whether change has occurred and determine if that change represents preshivering. Although the analyzer shown in FIG. 2 is a separate physical device, it may be incorporated into the same physical apparatus that contains the EMG device. Alternatively, it may be located as a separate device and indeed in a far distant location, for example in an emergency room where the EMG apparatus is in an ambulance in the field, or at a central nursing station where the EMG is in the hospital at bedside, and data is transmitted, perhaps wirelessly, between them.

Data representing one of the characteristics listed above may be sampled and sent to the analyzing device. When this is done in conjunction with cooling the subject, the data are initially sampled before subject cooling begins in order to arrive at a baseline value. As the subject cools, the data may be sampled at various times, for example initially every few minutes, and later more frequently, and when the situation dictates, for example when the subject shows the first sign of preshivering, or some other consideration such as a fixed time after sampling began, maybe thirty seconds or even more frequently. Generating and sampling data may not even be conducted after a baseline value has been determined until the subject has reached a certain body temperature nearing the shivering threshold.

Determination that any alteration of the value of the data, if any, represents change may be made by the analyzing device using algorithms employing the various mathematical methods for analyzing a data stream and comparing data points with a predetermined value, such as a nominal value for previous responses. Some of the mathematical and statistical tools that are useful for making such a determination are listed in the discussion in the background of the invention above.

The analysis device then may direct an action in response to that determination. Such actions may be many and include, to name just a few by way of example but not limitation: sounding an alarm at some location that will be noticed by health personnel that are treating the subject; generating a message, flashed on a screen observable by those personnel; generating instructions displayed on a screen to alter the treatment to the subject, for example reducing cooling rate or increasing anti-shivering efforts; generating automatic to a controller of a cooling system for automatic adjustments the hypothermia system; generating automatic instructions to a device controlling the administration of anti-shivering medication to increase or decrease anti-shivering drugs delivered to an IV drip, or the like.

Figure 3:
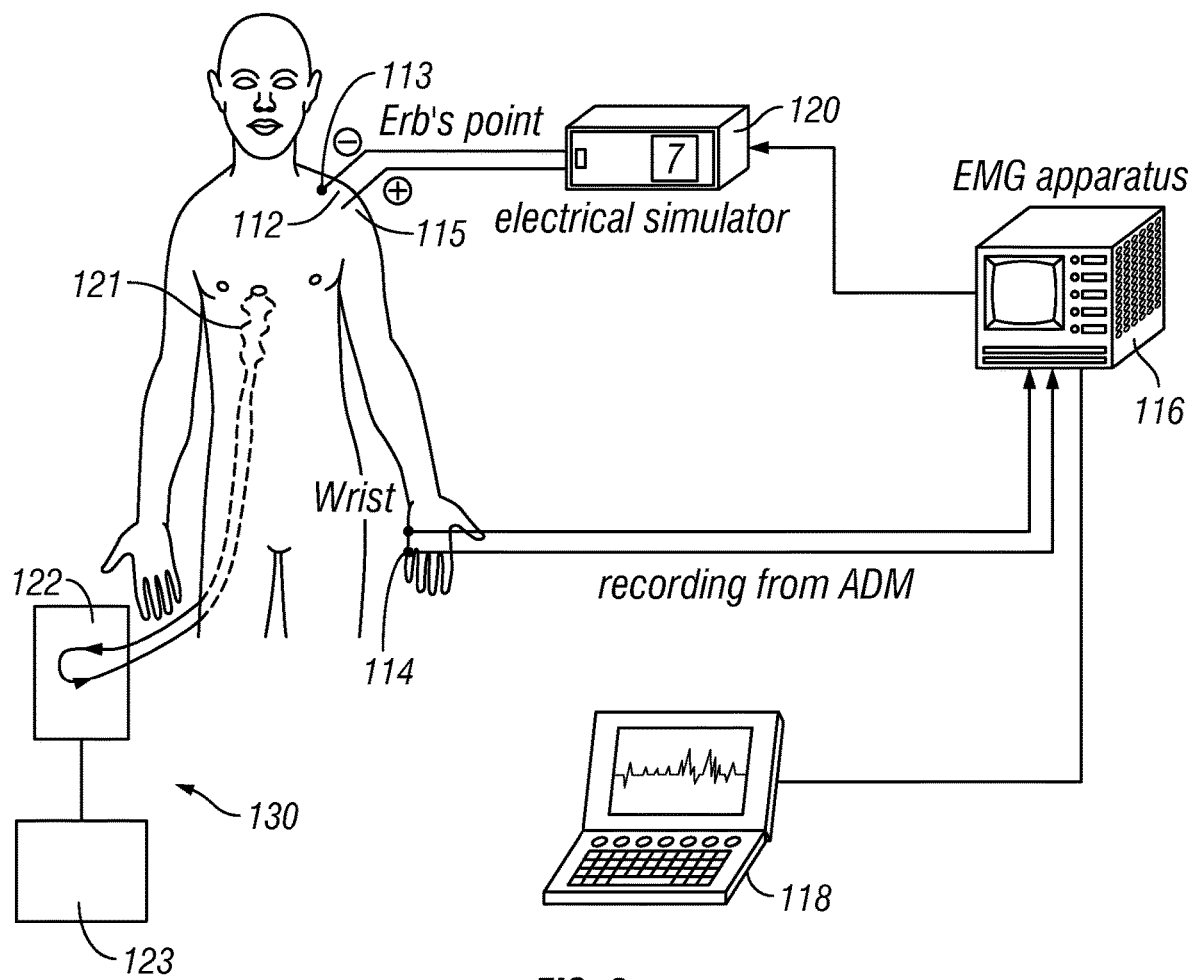
FIG. 3 is a depiction of another embodiment of the system of the invention with an electrical stimulator at Erb's Point on a subject.

Another embodiment is depicted in FIG. 3. In this embodiment, the stimulation is an electrical stimulation at the shoulder of the subject at Erb's Point 112. A cathode 113 on the front of the shoulder area and an anode 115 located on the back of the shoulder area are electrified by a current from an electrical stimulator 120 to stimulate the nerve that enervates the abductor digiti minimi. The electrical pulse generated by the electrical stimulator is triggered by a signal from the EMG 116. The resultant MEP at the abductor digiti minimi is detected by the sensor 114 and the data representing that MEP is directed to the EMG 116. That in turn is directed to the analyzing device 118 to be analyzed and compared to previous responses to determine if change has occurred and if so, if that change represents the appearance of preshivering. An appropriate action may then be determined, such as continued monitoring with no other action should no preshivering be detected, or if it is, a warning buzzer, a reduction in cooling rate, increase of anti-shivering mechanisms applied to the subject, and/or the like. The rate of future stimulations/responses can then also be determined. For example, if no change is present, it may be determined not to generate another MEP for 5 minutes, or if change representing preshivering is detected, and a reduction in cooling rate is instituted, it may be determined to generate the next MEP every 15 seconds until the preshivering goes away.

If the subject is being cooled, a cooling system comprising an internal heat exchanger such as a cooling catheter 121, an external heat exchange unit 122 such as a unit to heat or cool and circulate heat exchange fluid through the catheter and a controller 123 may be used.

Figure 4:
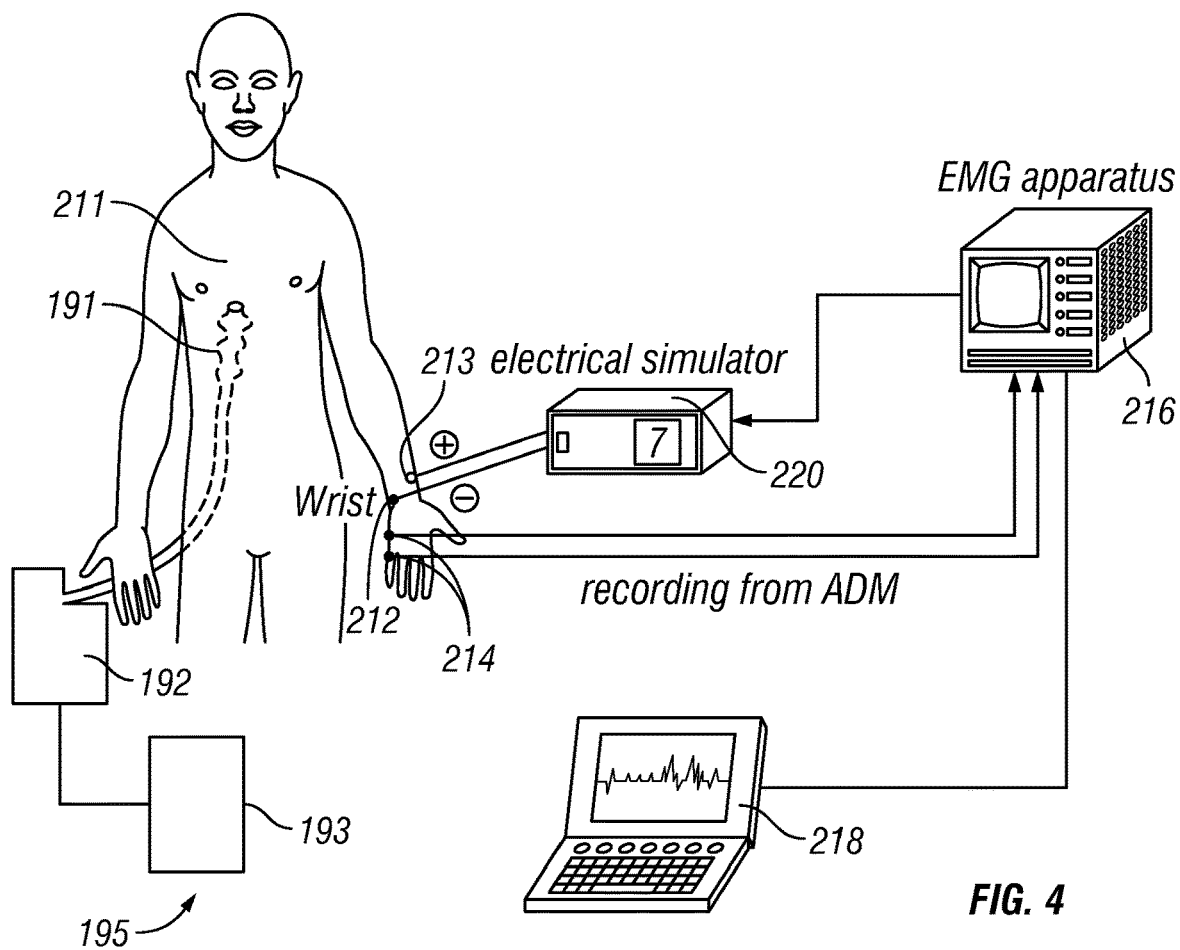
FIG. 4 is a depiction of another embodiment of the system of the invention with an electrical stimulator at the wrist of a subject.
Figure 7:
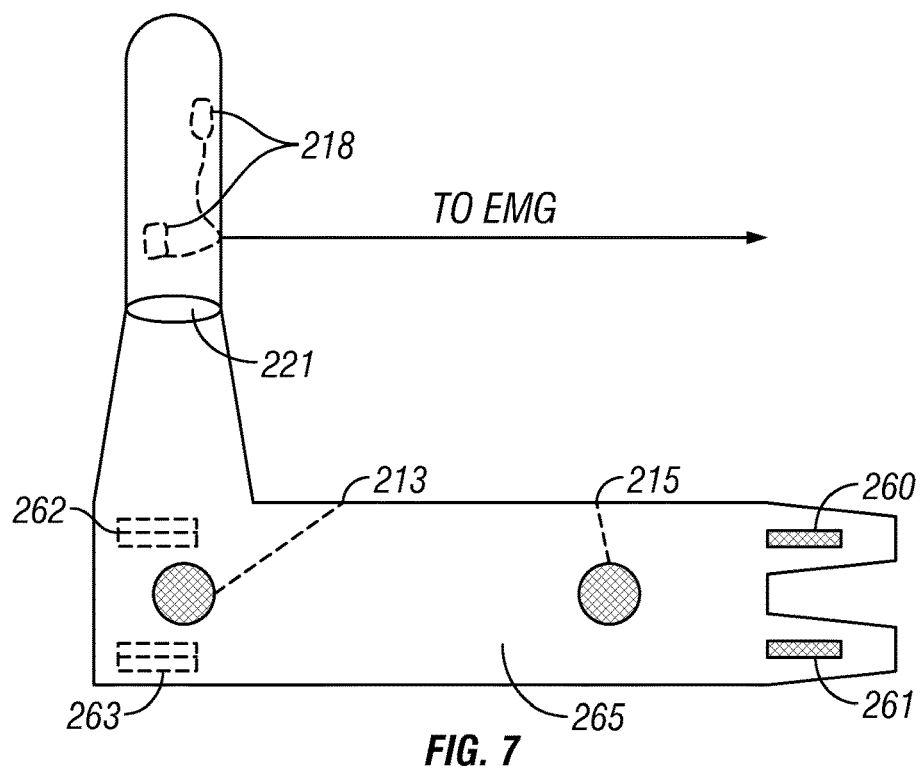
FIG. 7 is a depiction of a wrist wrap with finger cavity according to an example embodiment of the invention.

Another embodiment is shown in FIG. 4. This embodiment is similar to that shown in FIG. 3, except that the stimulation occurs by means of an electrode stimulator comprising an anode 212 located at the front of a wrist of the subject and a cathode 213 on the back of the wrist. The EMG apparatus 216 triggers a stimulating pulse generated by electrical stimulator 220 to the stimulator on the subject's wrist. It again triggers a response at the abductor digiti minimi which generates representative data that is directed back to the EMG apparatus. After the MEP is generated by the electrical stimulation, a sensor 214 detects data representing that MEP and the data is directed to the analysis device 218. The proximity of the stimulator and the detector has several advantages. It is a short neural pathway, advantageous because of the relatively short latency, because there is less likelihood of other stimulation of the pathway intervening or otherwise distorting the response. Also it may be advantageous for practical reasons, for example, the stimulator and the receptor can both be incorporated into a glove like device as shown in FIG. 7, having the sensor 214 located in a finger cavity 221. The electrical stimulator electrodes 213, 212 located on a wrist strap 266, attachment tabs 260,261,262,263 which may be for example, Velcro® to provide a convenient device for simply slipping onto the little finger of a subject, wrapping the wrist strap around the subject, and attaching the electrical connections. If the connections are all incorporated into a single plug, the entire attachment process can take place in very little time and with little effort; slip the finger into the finger cavity, wrap the wrist strap around and fasten it, and plug in the connections.

In this embodiment, if the subject is being cooled, a cooling system 195 comprising an internal heat exchanger such as a cooling catheter 191, an external heat exchange unit 192 such as a unit to heat or cool and circulate heat exchange fluid through the catheter and a controller 193 to direct and control the system may be used.

Figure 6:
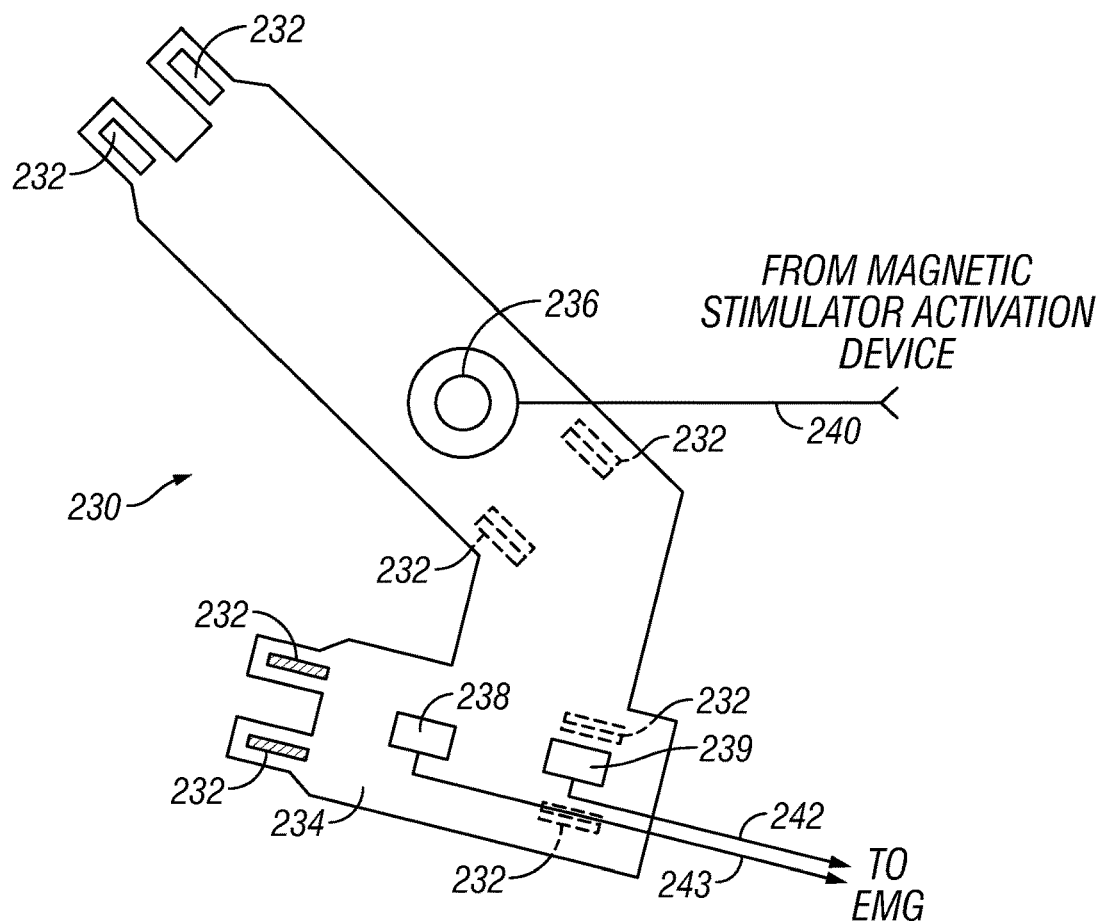
FIG. 6 is a depiction of a strap for use with one embodiment of this invention.

In another embodiment, not illustrated, the system comprises a magnetic stimulator placed over the shoulder blade to stimulate Erb's Point. This may stimulate the abductor digiti minimi or may stimulate the bicep or triceps. A circular magnetic stimulator may be employed, or a FIG. 8 magnetic stimulator (also sometimes called a butterfly magnetic stimulator) may be applied. (The later provides a more focal location for the nerve stimulation and may be helpful in stimulating Erb's Point effectively since the area is a plexus with many closely spaced nerve pathways.) The MEP generated is sensed and analyzed in the same general manner as was described above. Because of the proximity of Erb's point to the location on either bicep or triceps for sensing the nerve conduction, one convenient embodiment incorporates a magnetic stimulator for Erb's Point stimulation and the sensors into a single strap which could be placed across a subject's body and rapidly fastened. FIG. 6 shows such a strap 230 configured to encircle a subject's shoulder having Velcro® attachments or snaps and an additional area, also fastened with Velcro® or snaps that could be fastened around the subject upper arm to sense, depending on the location of the sensor, the bicep or triceps to sense a response from a stimulation. A magnetic stimulator 236 embedded in the portion to be strapped around the subject's shoulder is located over Erb's Point when that portion of the strap is fastened around the shoulder. Sensing electrodes 238,239 are located over the bicep and triceps when that portion of the strap is wrapped around the subject's arm. (Since the stimulation may cause an MEP at either the bicep or triceps, and it may not be possible to determine with the necessary precision where to place the stimulator to cause the reaction in which particular site, having sensors at both allows the analysis device to determine from the first few responses sensed where the strongest MEP is being generated. The analysis device may then dictate which site is being used to sense the MEP for a particular case. Since the details of exactly where the MEP is sensed is not critical, what is important is that the MEP be readily detectable and consistent unless a physiological change indicating preshivering occurs, the system is free to choose the site being used in a particular occasion.) A device (not illustrated) which triggers the magnetic stimulator is attached to the magnetic coil and the sensor are attached to the EMG (also not illustrated) by connectors 240, 243.

In the above described embodiments, MEPs are generated that have pulse width, latency, and amplitude. It will readily be appreciated by those of skill in the art that a sophisticated analysis device would be capable of analyzing more than one characteristic of the data and using more than one in making a determination of preshivering. For example, if the subject is comatose but in the process of being revived, a change in amplitude of the MEP might not indicate preshivering if there is no change whatsoever in latency. In such a case, if the analysis device is using both amplitude and latency for its determination, the determination might be that no preshivering exists, where if only the amplitude were analyzed, a false positive of the existence of preshivering might be the determination. In addition to latency, amplitude and pulse width the refractory period may be determined and analyzed, although this will be significantly more difficult to combine with the other factors since the method of determining refractory period involves generating series of pulse that by definition affect each other in their characteristics. Still, this characteristic of the neural transmission of the subject may be determined and combined with the other data to make a determination of preshivering.

Another embodiment involves magnetically stimulating the phrenic nerve roots and monitoring resultant twitch pressure. The resultant twitch pressure may be diaphragm pressure, esophageal pressure or gastric pressure, each of which may be useful in determining the diaphragm's twitch response, essentially equivalent to the motor evoked potential of the other locations described above. This embodiment may be particularly useful for subject's being cooled by an intravascular system in a hospital setting. Many of those subjects have an esophageal temperature probe which senses esophageal temperature and provides this temperature to the controller of the intravascular system to provide subject temperature for control purposes. If a pressure sensor is included in the esophageal catheter which carries the temperature probe, and the same electrical cable which attaches the temperature probe to the controller may attach the esophageal pressure sensor to the controller. If the controller houses a processor that may be programmed to compile and analyze the esophageal pressure data to detect and analyze whether a change has occurred and if that change signifies preshivering, that same controller may be programmed to respond to that determination by, for example, slowing the rate of cooling, stopping cooling, or even warming the subject to prevent actual shivering from taking place.

Figure 5:
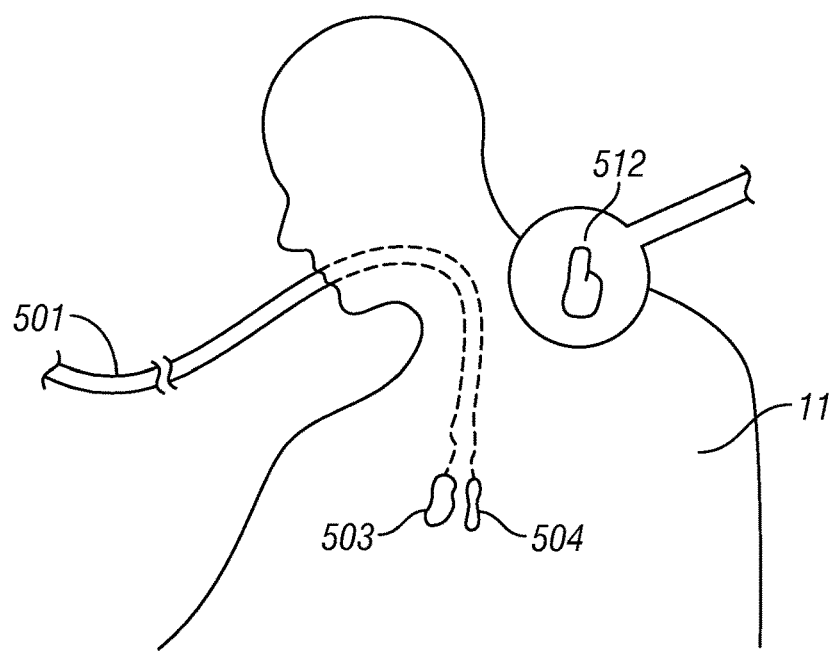
FIG. 5 a depiction of another embodiment of the system of the invention with a magnetic stimulator over the neck of a subject.

An example of this embodiment is depicted in FIG. 5. A circular magnetic stimulator 512 is positioned over the spinous process at C5-C6 with the neck slightly flexed. This can be accomplished in an unconscious subject by placing a pillow or the like below the head of a prone subject and locating the magnetic stimulator as shown in FIG. 5. An appropriate commercially available magnetic stimulator for this purpose is the Magstim 200™ (Magstim Cdo. Ltd, Whistlan d, Dyfed, Wales, UKL) with a circular 90 mm coil (maximum output 2.5 Tesla.) An esophageal catheter 501 having at least two lumens is inserted into the subject's esophagus. One lumen of the catheter comprises a balloon pressure sensor 503. The balloon sensor may be at the end of one lumen of a two lumen esophageal catheter 501, and the other lumen may carry an esophageal temperature probe 504. This provides a measure of esophageal pressure, show at 601 in FIG. 8. Alternatively, gastric pressure 603 may be taken with a balloon pressure sensor on a latex catheter inserted in the stomach, or the pressure from the lungs which would more directly measure the diaphragm twitch pressure, 605. The twitch as exhibited in an increase in lung pressure might be detected by, for example, a pressure sensor located in a breathing mask such as an oxygen mask, or some sensor inserted into the trachea, or over the mouth if nose clips are attached. These can then be used directly as the equivalent of MEP amplitude to identify and characterize change which would indicate preshivering.

There is significant redundancy in the muscle groups that are capable of generating breathing. In addition to the diaphragm, which is the primary mechanism, the intercostal muscles, and various back and neck muscles and abdominal muscles when stimulated alone or in various combinations can cause increases or decreases in intrathoracic pressure that can be measured by the esophageal, tracheal or gastric probes. Measurements of changes in pressure waveform amplitude as well as other pressure waveform morphological characteristics such as pulse width, etc. would be an especially sensitive way to measure the change in muscle tone of that region and detect preshivering. Since the torso is a portion of the body where shivering tends to occur earlier than some other places, detecting preshivering here could be especially useful.

Other placements of stimulators and sensors are possible with analysis occurring in much the same manner. For example, magnetic stimulation over the lumbosacral region evokes MEPs in the lower limbs. It may be desirable to use this location if, for example, a subject is being resuscitated in an ambulance with the use of shock paddles and ECG sensors, or the chest and arms are involved in treatment such as drug treatment or heart massage or resuscitative breathing treatment, or cooling is in progress, so but access to the chest and arms is limited. A round coil placed over the lumbar spinal column tends to activate the spinal nerve some 3.0 ms or 15 cm distal to the motor neuron when they are stimulated over the motor cortex. This causes an increases in the latency measured using this location. However this increase in latency due to that placement is unimportant for our purposes. What is important is whether the resultant MEPs remain consistent with each other unless there is a change in the physiological condition of the subject that indicates that preshivering has occurred.

Figure 8:
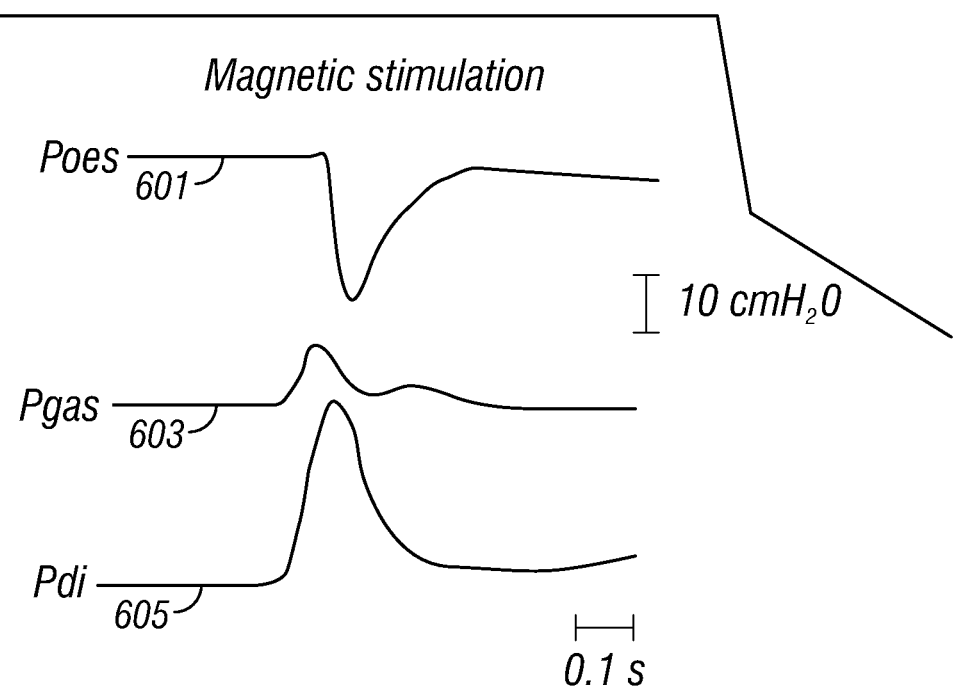
FIG. 8 is a depiction of the pressures that may be measured in the embodiment shown in FIG. 5.

In another magnetic stimulator placement, a FIG. 8 coil placed over the distal caudate equine tends to excite the lumbar roots if the junction is oriented horizontally, and the sacral roots if the junction is oriented vertically. This too may be useful if other locations are unavailable or otherwise undesirable.

In the case of either a circular magnetic stimulator or a FIG. 8 stimulator, where a subject is in a supporting device such as a backboard or a mechanical resuscitation device, the magnetic stimulator may be built into the device. One such device used to resuscitate cardiac arrest victims is the AutoPulse® manufactured by ZOLL Circulation. When that device is strapped onto a subject, a built-in magnetic stimulator could be located so that it is properly positioned on the subject, and a sensor may be attached to the appropriate location, for example the leg of the subject. The sensors might be separate from the device, but might also be attached to it by a strap or the like. The sensors may also be contained in, for example, a leg wrap with adhesive attachments, similar to the wrist wrap described above. With a built in magnetic stimulator, and sensors readily attached to the subject, the system may be fully attached if the EMG with magnetic stimulator trigger and analysis device has appropriate plugs that mate with plugs from the stimulator and sensors.

Figure 11:
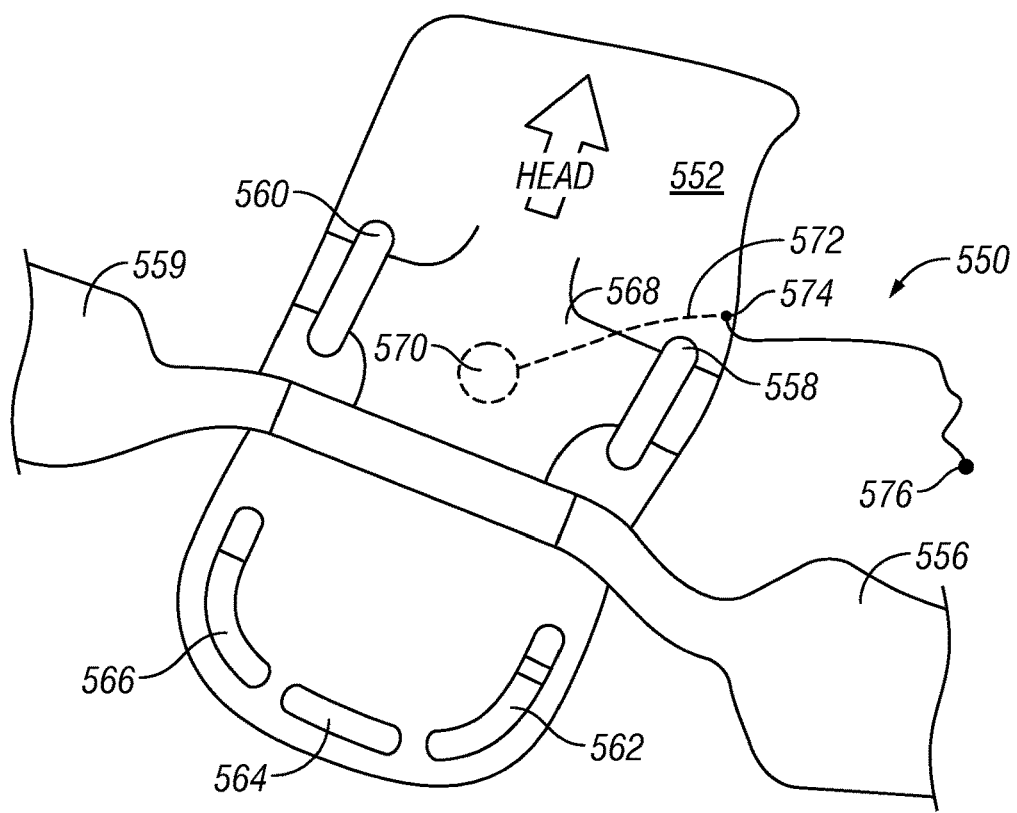
FIG. 11 is a depiction of another embodiment of the invention including a back board.
Figure 12:
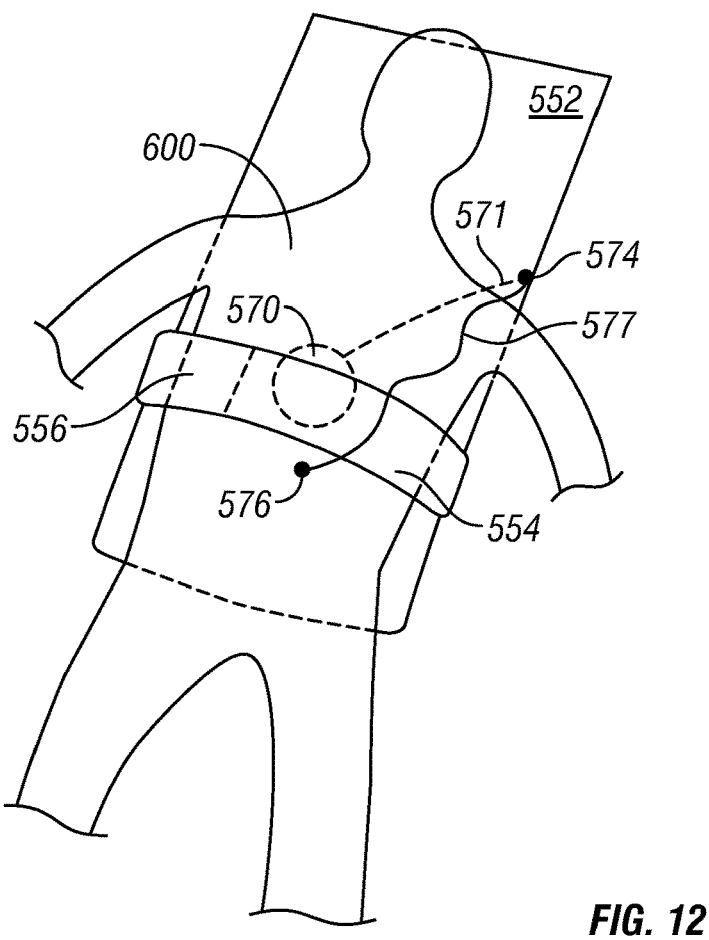
FIG. 12 depicts the embodiment of FIG. 11 as attached to a subject.

An embodiment using a built-in stimulator is shown in FIG. 11 and FIG. 12. In this embodiment, a magnetic stimulus to the T1-T11 spinal area elicits a response of the rectus obdominis. The embodiment shown is for use with a victim of cardiac arrest that is being resuscitated using an automatic cardio-pulmonary device such as the AutoPusle® manufactured by ZOLL Medical. Such a resuscitation backboard as used in this embodiment comprises, for example, a rigid plate 552 to place behind the victim's back, straps 554, 556 for fastening around the chest of the victim to apply periodic constrictions to aid resuscitation. The board may have cutouts 558, 560, 562, 564, 556 to function as hand grips or the like. An outline of a body 568 helps to locate where the victim is to be placed during resuscitation. A magnetic stimulator 570 is embedded in the baseplate 552. A connecting wire 572 is also embedded into the board and connects to a plug that may receive a reciprocal plug for electrical activation by an EMG or like control unit. A sensor also connects to the plug. The sensor is for placement on the victim's rectus abdominis to sense MEPs generated and transmit those sensed responses via a connecting wire 577 from magnetic stimulations to the T1-T11 when those stimulations are delivered. It should be noted that, although for convenience in the example illustrated both the magnetic stimulator and the sensor are electrically attached to a plug in a common physical area for ease of electrical attachment, this requires a specialized plug that is able to segregate signals from the two devices. Alternatively the two can be entirely separate. Indeed the sensor need not be attached to the resuscitation board in any manner.

In use, illustrated in FIG. 12, cardiac arrest victim 600 is placed on an auto resuscitation backboard 552 and the two ends of the resuscitation strap 556,554 are fastened over the lower chest area of the victim. This positions the magnetic stimulator under the thoracic region of the victim. A sensor 576 is fastened to the subject over the rectus abdominis. Magnetic stimulation to the thoracic spine generates a response which may be analyzed as described in the previous embodiments.

Figure 13:
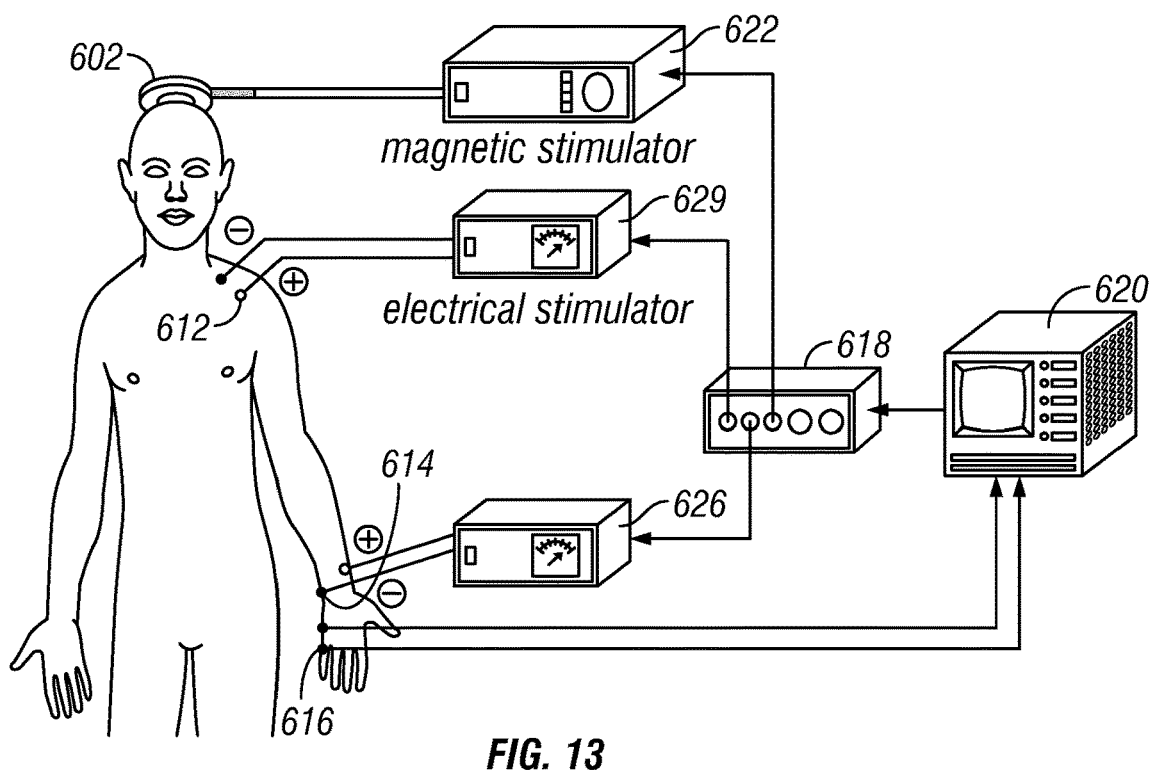
FIG. 13 is a depiction of an embodiment for a triple stimulation technique.

MEPs may be generated for analysis using the Triple Stimulation Technique. Illustrated in FIG. 13, a subject is stimulated in three locations, a magnetic stimulator over the motor cortex 602, electrical stimulation over Erb's Point 612, and electrical stimulation over the wrist 614. The sensor 616 detects the resultant MEP in the abductor digi minimi. The MEP is evoked by a series of timed stimulations. The stimulations are generated in response to a signal from the EMG 620 that signals a timer 618 to trigger a series of specially timed signals to a magnetic stimulator 622, an electrical stimulation generator for Erb's point 624, and an electrical stimulation generator for the wrist 626. The stimulations are timed so that the descending nerve signals collide to create response at the ADM that may be analyzed as described above to detect change that indicates preshivering. The collisions are timed to cancel out the contributions from the upper motor neurons, allowing an MEP that is uniquely representative of primarily the lower motor neurons and provides a unique signal for analysis.

Figure 9:
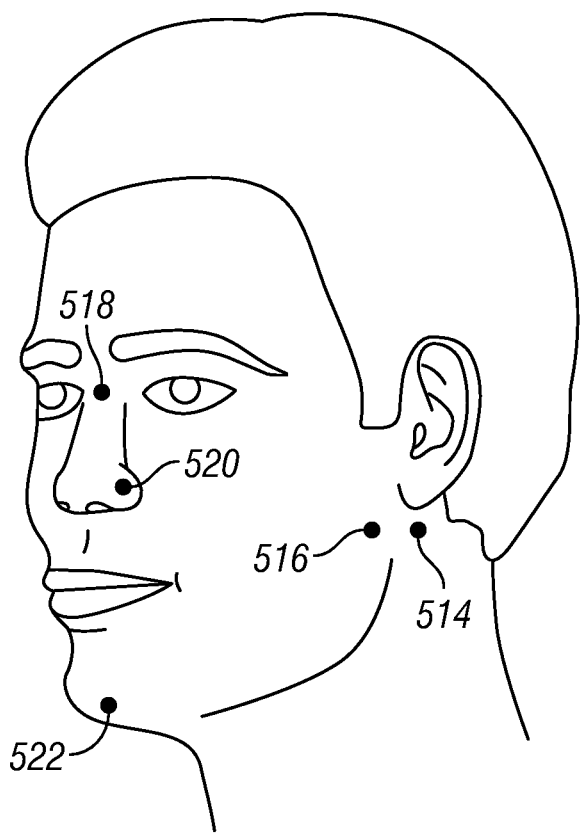
FIG. 9 is a side view of the face of a subject indicating points of potential stimulation or sensing according to an example embodiment of the invention.

In another embodiment, a magnetic coil placed at various sites over the head will evoke MEPs on the face that may be detected at the ipsilateral nasalis muscle. (In some cases, the nature of the stimulation and the evoked response is traditionally called a compound muscle action potential, or CMAP, but for our purposes it is essentially the same as an MEP, comprising a signal sensed at the muscle in response to a stimulation on the nerve pathway that activates that muscle, so no distinction is made in this patent.) Referring to FIG. 9, a subject may be stimulated either just posterior, 514 or anterior 516 of the ear. The sensors may be attached to the left ipsilateral nasalis 520 or the right ipsilateral nasalis, and may have grounds attached at the chin 522 and a reference sensor or on the superior aspect of the nose 518 away from the facial muscles. The stimulator may be electrodes or butterfly magnetic stimulators. Because of the proximity of the stimulation sites and the sensing sites, a mask with the necessary sensors and stimulators can be devised. Such a mask may leave the airways clear for resuscitation efforts, but especially when the subject is being cooled in the hospital, may be closed and even incorporated into an oxygen mask or breathing gas mask.

Figure 10:
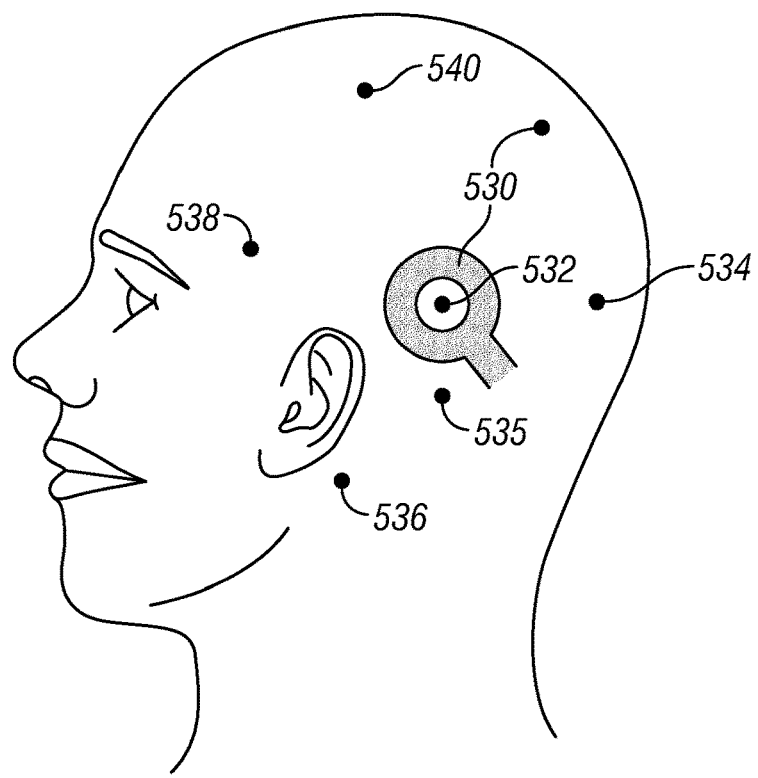
FIG. 10 is a side view of the head of a subject indicating points of potential stimulation according to an example embodiment of the invention.

FIG. 9 shows one location for a stimulation/response where facial response is available. FIG. 10 shows a series of locations 532, 534, 536, 538, 540 where a circular magnetic stimulator 530 has been confirmed to generate MEPs on the face, as well as midpoints between those locations. When placed at 532 it generates the strongest response, but as can be seen, a cap with a single circular magnetic stimulator on it will generate a detectable MEP in almost any location on the head. Such a cap is therefore a handy method of generating a series of MEPs to create the stream of data for analysis as described above to detect preshivering. As noted above, a number of sensors may be placed, and after the first few stimulations, the analysis device can determine which of the sensors is receiving the most consistent and strongest signal, and select that sensor for use in the subsequent MEP detection and analysis. It is generally not the absolute value of the latency or pulse width or amplitude or refectory period that is important, it is the appearance of change that signals preshivering.

An additional advantage to most of these methods described above is the ability to identify when neural function returns after a period during which the subject is essentially moribund. Since these systems will often be attached to the subject that has suffered a cardiac arrest, in anticipation of cooling that subject, and may be incorporated into resuscitation equipment for use in such a situation, a subject may be sampled initially for any neural response. When no such response is present, that is when stimulation generates no MEP whatsoever, the system may wait a predetermined period, and stimulate the subject again. This may continue until the subject begins to show an MEP in response to a stimulation. This process is generally available using any of the embodiments discussed above. When the subject begins to show a reliable MEP in response to stimulation, cooling may be begun and the system may then monitor for preshivering.

An aspect of the invention further provides novel methods and systems of creating nerve conduction data and determining if preshivering exists.

An aspect of the invention further provides novel methods of collecting data describing the amplitude of an MEP from a stimulation of a subject being cooled and determining if preshivering exists.

An aspect of the invention further provides methods of collecting data describing the response width of an MEP from a stimulation of a subject being cooled and determining if preshivering exists.

An aspect of the invention provides methods of collecting data describing the latency of an MEP from a stimulation of a subject being cooled and determining if preshivering exists.

An aspect of the invention further provides methods of collecting data describing the refractory period of a nerve from a stimulation of a subject being cooled and determining if preshivering exists.

An aspect of the invention comprises methods of analyzing the data to detect preshivering. The method comprises generating a data stream, e.g. a series of MEPs, and analyzing that data to identify change that indicates preshivering.

An aspect of the invention comprises methods of analyzing the data to detect preshivering wherein the method comprises generating a data stream, e.g. a series of MEPs, and analyzing that data to identify change that indicates preshivering using a mathematical method chosen from the group of methods comprising mean, mode, auto-regressive moving average, change point analysis techniques such as Basseville, Schuhart, Kalman estimation, particle filters.

An aspect of the invention provides methods of creating a data stream of MEPs representing stimulation by an electrical stimulator and analyzing that data stream to identify preshivering.

An aspect of the invention provides methods of creating a data stream of MEPs representing stimulation by magnetic stimulator and analyzing that data stream to identify preshivering.

An aspect of the invention provides methods of creating a data stream of MEPs representing stimulation in the area of Erb's point and sensing in the area of the abductor digiti minimi and analyzing that data stream to identify preshivering.

An aspect of the invention provides methods of creating a data stream of MEPs representing stimulation in the area of the wrist and sensing in the area of the abductor digiti minimi and analyzing that data stream to identify preshivering.

An aspect of the invention provides methods of creating a data stream of MEPs representing magnetic stimulation in the area of the motor cortex and sensing in the area of the abductor digiti minimi and analyzing that data stream to identify preshivering.

An aspect of the invention provides methods of creating a data stream of MEPs representing stimulation in the area of Erb's point and sensing in the area of the bicep and analyzing that data stream to identify preshivering.

An aspect of the invention provides methods of creating a data stream of MEPs representing stimulation in the area of Erb's point and sensing in the area of the triceps and analyzing that data stream to identify preshivering.

An aspect of the invention provides methods of creating a data stream of representing stimulation in the area of the T1-T12 spinal nerves and sensing in the area of the rectus abominis and analyzing that data stream to identify preshivering.

An aspect of the invention provides methods of creating a data stream of MEPs from magnetic stimulation of the phrenic nerves and analyzing that stream of data to identify preshivering.

An aspect of the invention provides methods of generating, collecting and analyzing data describing the nerve velocity data resulting from use of triple stimulation technique on a subject being cooled and determining if that subject has preshivering.

An aspect of the invention provides for generating data, collecting that data, analyzing that data, identifying that data that indicates preshivering, and responding in a way that works to reduce the chance that shivering will begin. Such methods of generating, collecting and identifying that data which indicates preshivering include for example, stimulating a nerve, sensing the muscle response from that stimulation, obtaining data representing that response, analyzing that data, and identifying that data which indicates preshivering, and responding to reduce the likelihood that shivering will begin. Methods of responding include, for example: controlling the method of gathering or data, such as controlling the rate of sampling data, analyzing different or additional characteristics of the responses (e.g. latency, amplitude, width); generating an audio signal; generating a visual signal; issuing instructions to a controller of a system controlling the application of therapeutic hypothermia; and other useful responses.

An aspect of the invention includes methods to transmit the preshivering information for use in providing therapeutic hypothermia treatment. For example, by way of example and not limitation, by wireless transmission from an ambulance to a hospital while a subject is being transported from the scene of a medical emergency to a hospital for treatment that includes therapeutic hypothermia, or by direct connection to the controller of a therapeutic hypothermia system to control rate of cooling or target temperature for the therapeutic hypothermia system.

An aspect of the invention comprises a method including a response to the determination that preshivering exists that includes administering an anti-shivering agent. This may be one or a combination of several agents. These include: a drug or a combination of drugs, or a substance of a certain temperature, such as a warmed IV substance. The timing and amount of this may vary, and may be adjusted based on specific information input, such as the condition of the subject, the weight of the subject, the length of time that the anti-shivering agent will be needed, previous responses of the subject to anti-shivering agents already administered, and the like.

An aspect of the invention comprises a method that includes providing a visual signal that preshivering exits. Such a signal includes a warning light, a data read-out, signal on a data screen, or other visual signal. Such a signal may allow or instruct the health care personnel to take further measures such as stopping cooling, actively warming, administering anti-shivering efforts, and increasing observational vigilance.

An aspect of the invention comprises a method that includes providing an auditory signal that preshivering exits. This may be, for example an alarm, a buzzer, verbal auditory message, or the like. As with the visual signal, this will allow responses by the care giver of the subject. It may be combined with visual signals to provide instruction for treatment adjustments.

An aspect of the invention comprises providing a method of cooling of a subject, and includes a response to the determination of preshivering that includes manual adjustment of cooling rate of a subject.

An aspect of the invention comprises a system providing for determining whether preshivering exists and responding to that determination comprising a device for generating physiological data, a device for collecting that data, a device to analyze that data received to determine preshivering exists, and a mechanism for responding to that preshivering.

An aspect of the invention comprises a system for determining whether preshivering exists and responding to that determination comprising a stimulator, a sensor for receiving and monitoring a response resulting from that stimulation, a device for collecting and compiling data representing that response, device for analyzing the data to determine if change has occurred, and a means of acting in response to that determination.

An aspect of the invention comprises a system for determining whether preshivering exists and responding to that determination comprising a stimulator, a sensor for receiving and monitoring a response resulting from that stimulation, a device for collecting and compiling data representing that response, device for analyzing the data to determine if change has occurred, and a means of acting in response to that determination, where the sensor detects an MEP resulting from the stimulation of a nerve, and the data representing that response is the amplitude of the MEP.

An aspect of the invention comprises a system for determining whether preshivering exists and responding to that determination comprising a stimulator, a sensor for receiving and monitoring a response resulting from that stimulation, a device for collecting and compiling data representing that response, device for analyzing the data to determine if change has occurred, and a means of acting in response to that determination, where the sensor detects an MEP resulting from the stimulation of a nerve, and further including a timer for determining the time between the stimulation and the MEP (latency) and where the data representing the response is the latency, and wherein change representing preshivering is change in the latency.

An aspect of the invention comprises a system for determining whether preshivering exists and responding to that determination comprising a stimulator, a sensor for receiving and monitoring a response resulting from that stimulation, a device for collecting and compiling data representing that response, a device for analyzing the data to determine if change has occurred, and a means of acting in response to that determination, where the sensor detects an MEP resulting from the stimulation of a nerve, and further including a timer for triggering said stimulator, where the timer is capable of generating a series of closely spaced stimulations at shorter and shorter intervals until it reaches an interval so short that no MEP is detected in response to the stimulation.

An aspect of the invention comprises a system for determining whether preshivering exists and responding to preshivering comprising a system including a stimulator, a timer for triggering the stimulation, a sensor for receiving data including a the time between the stimulation and the response, a device for collecting and compiling the data including the time between the stimulation and the response, device for analyzing the data to determine if change has occurred in latency between the most recent response or group of responses and previous responses, and a means of responding to the determination.

An aspect of the invention comprises a system for determining whether preshivering exists and responding to preshivering comprising a system including a stimulator, a timer for triggering the stimulation, a sensor for receiving data including a the time between the stimulation and the response, a device for collecting and compiling the data including the time between the stimulation and the response, device for analyzing the data to determine if change has occurred in latency between the most recent response or group of responses and previous responses, and a means of responding to the determination whether change has occurred, where the response generated is an auditory signal. By way of example but not limitation, the signal may be a warning buzzer, a bell sound, a auditory verbal message or the like.

An aspect of the invention comprises a system for determining whether preshivering exists and responding to preshivering comprising a system including a stimulator, a timer for triggering the stimulation, a sensor for receiving data including a the time between the stimulation and the response, a device for collecting and compiling the data including the time between the stimulation and the response, device for analyzing the data to determine if change has occurred in latency between the most recent response or group of responses and previous responses, and a means of responding to the determination whether change has occurred including a system containing a controller for controlling the temperature of said subject, said controller receiving data that indicates preshivering, and said controller responding to data indicating preshivering.

An aspect of the invention comprises a system for determining whether preshivering exists and responding to preshivering comprising a system including a stimulator, a timer for triggering the stimulation, a sensor for receiving data including a the time between the stimulation and the response, a device for collecting and compiling the data including the time between the stimulation and the response, device for analyzing the data to determine if change has occurred in latency between the most recent response or group of responses and previous responses, and a means of responding to the determination whether change has occurred including a system containing a controller for controlling the temperature of said subject, said controller receiving data that indicates whether preshivering is present, said controller responding to that data, said response automatic without manual intervention.

An aspect of the invention comprises a system for determining whether preshivering exists and responding to preshivering and including an active cooling device and controller, where the controller controls the cooling rate of the cooling device, and the response to the determination is to adjust the cooling rate by the controller.

An aspect of the invention comprises a system for determining and responding to preshivering and preshivering and including a system for automatically controlling the temperature of a subject, said system having a controller, and where the system for automatically controlling the temperature of the subject is capable of positive warming of the subject, and where the controller controls the warming rate provided by the temperature control system, and the response to the determination of preshivering is to begin active warming of the subject.

An aspect of the invention comprises a system for determining whether preshivering exists and responding to that determination comprising a system including a plurality of stimulators, a timer for triggering the stimulations, a sensor for receiving data representing the response to the stimulation including a the time between at least one stimulation and the response, a device for collecting and compiling the data, and device for analyzing the data to determine if change has occurred in the time of response between the most recent response or group of responses and previous responses, and a means of responding to the determination whether a change has occurred.

An aspect of the invention comprises a system for determining whether preshivering exists and responding to that determination comprising a device for receiving physiological data from a subject undergoing cooling, a means to analyze the data received to identify a portion of the data that indicates preshivering, a mechanism for responding to that preshivering portion of the data, and said system containing a cooling device for actively cooling a subject, said cooling device containing a controller for controlling the cooling provided by said device, said controller receiving a signal from the system that indicates preshivering, said controller automatically responsive to that signal, and further comprising an additional determination of the continued presence of preshivering after the response has been initiated, and periodically adjusting a response based upon determination of the continued presence of preshivering.

An aspect of the invention comprises a system for determining whether preshivering exists and responding to that determination comprising a stimulator, a sensor for sensing the response to said stimulation and generating data, a receiving and analyzing device for receiving and analyzing the data to identify data that indicates preshivering, and a mechanism for responding to that determination, where the sensor, the monitor, the receiving device, the analyzing device, and the mechanism for responding, may be connected remotely from at least one of the others, either wirelessly or by direct connection. By way of example but not limitation, a central processing system might receive data from a distal sensor or sensor monitor attached to a subject in an ambulance in the field, analyze that data, and send a signal to the ambulance that flashed a warning light to the operators in the ambulance, in response to which they might, by way of example, stop cooling the subject, start warming the subject, or take other measures. Similarly, a system for generating the data may be located in one facility or area of the facility whereas a central processing and analyzing unit may be located in another facility or some other area of the facility, and the data may be transferred from the data generating unit to the data processing unit, for example from an ICU to a nurses station.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Accordingly, the scope of the invention should be determined with reference to the appended claims and with the full range of equivalents to which those claims are entitled.

Furthermore, although the invention has been described hereabove with reference to certain specific examples or embodiments of the invention, any elements, steps, members, components, compositions, reactants, parts or portions of one embodiment or example may be combined with, incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

What is claimed is:

1. A system for cooling a subject's body and determining whether the subject begins to exhibit a stimulus-induced preshivering muscle tone which precedes the onset of shivering, the system comprising:
   a subject cooling device;
   a stimulator for stimulation of a nerve of a subject;
   a sensor for sensing a muscular response which results from stimulation of a nerve of the subject by said stimulator and for generating data representing at least part of that response;
   an analyzer which determines, on the basis of said data, whether said response is indicative of the presence of preshivering muscle tone which precedes the onset of shivering; and
   a controller which communicates with the analyzer and is programmed to act in response to a determination by the analyzer that said response is indicative of the presence of a preshivering muscle tone which precedes the onset of shivering.

2. A system as in claim 1, wherein said sensor comprises an EMG machine.

3. A system as in claim 1, wherein said analyzer comprises a programmable computer.

4. A system as in claim 1, wherein the cooling device comprises an endovascular cooling system.

5. A system as in claim 1, wherein the cooling device comprises a surface cooling device.

6. A system as in claim 1, wherein the controller is programmed to act in response to a determination by the analyzer that said response is indicative of the presence of a preshivering muscle tone which precedes the onset of shivering by actuation of a component by causing an event selected from; reducing a rate of cooling by the subject cooling device, stopping cooling by the subject cooling device, initiating an anti-shivering mechanism, increasing an anti-shivering mechanism, sounding an alarm, providing a visual alert, and transmitting a signal to a control unit which controls said subject cooling device.

7. A method for using a system of claim 1, the method comprising:
   using the subject cooling device to cool the subject's body;
   using the stimulator to stimulate a nerve of the subject;
   using the sensor to sense a muscular response which results from said stimulation of a nerve of the subject by said stimulator and generating data representing at least part of that response;
   using the analyzer to determine, on the basis of said data, whether said response is indicative of the presence of preshivering muscle tone which precedes the onset of shivering; and
   using the controller to cause an act in response to a determination by the analyzer that said response is indicative of the presence of a preshivering muscle tone which precedes the onset of shivering.

8. A method as in claim 7, wherein using the subject cooling device to cool the subject's body comprises using infusion apparatus to infuse cold IV fluid.

9. A method as in claim 7, wherein using the subject cooling device to cool the subject's body comprises using an intravascular cooling system to cool the subject's body.

10. A method as in claim 7, wherein the analyzer performs an analyzing method selected from: mean, mode, autoregressive moving average, change point analysis, Basseville analysis, Schuhart analysis and Kalman estimation analysis.

11. A method as in claim 7, wherein the controller is used to cause an act is selected from the group comprising: reducing a rate of cooling by the subject cooling device, stopping cooling by the subject cooling device, initiating an anti-shivering mechanism, increasing an anti-shivering mechanism, sounding an alarm, providing a visual alert, and transmitting a signal to a control unit which controls said subject cooling device.

12. A method as in claim 7 wherein the sensor and the stimulator are located on a body support board or automatic resuscitation unit and wherein the subject is placed on the body support board or automatic resuscitation unit such that the stimulator and said sensor are automatically positioned at respective operative positions on the subject's body.

13. A system according to claim 1 wherein the stimulator is used to deliver a number of successive simulations of the nerve and wherein the analyzer analyzes changes in a refractory period of the nerve following said successive stimulations.

14. A system according to claim 1 wherein the stimulator is used to deliver a number of successive simulations of the nerve and wherein the analyzer analyzes changes in pulse width, latency or amplitude of muscle evoked responses (MEPs) resulting from said successive stimulations sensor senses.

* * * * *